(12) United States Patent
Richter et al.

(10) Patent No.: US 9,512,097 B2
(45) Date of Patent: Dec. 6, 2016

(54) PROCESS FOR THE PREPARATION OF 3-AROYL-5-AMINOBENZOFURAN DERIVATIVES

(75) Inventors: Frank Richter, Kundl (AT); Erwin Schreiner, Kundl (AT); Samo Pirc, Ljublijana (SI); Anton Copar, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 0 days.

(21) Appl. No.: 13/884,179

(22) PCT Filed: Nov. 11, 2011

(86) PCT No.: PCT/EP2011/069974
§ 371 (c)(1),
(2), (4) Date: Aug. 15, 2013

(87) PCT Pub. No.: WO2012/062918
PCT Pub. Date: May 18, 2012

(65) Prior Publication Data
US 2013/0317100 A1 Nov. 28, 2013

(30) Foreign Application Priority Data
Nov. 12, 2010 (EP) .................................. 10191060

(51) Int. Cl.
C07D 307/00 (2006.01)
C07D 307/81 (2006.01)
C07D 307/82 (2006.01)
C07D 307/84 (2006.01)
A61K 31/343 (2006.01)

(52) U.S. Cl.
CPC ............ *C07D 307/81* (2013.01); *A61K 31/343* (2013.01); *C07D 307/82* (2013.01); *C07D 307/84* (2013.01)

(58) Field of Classification Search
CPC  C07D 307/87; C07D 307/81; C07D 307/84; A61K 31/343
USPC ........................................................ 549/467
See application file for complete search history.

(56) References Cited

U.S. PATENT DOCUMENTS 5,223,510 A * 6/1993 Gubin et al. .................. 514/299

FOREIGN PATENT DOCUMENTS

WO  WO 2009/044143 A2  4/2009
WO  WO 2010/040261 A    4/2010

OTHER PUBLICATIONS

Roger Adams et al., "Quinone Imides. XXXIX. Adducts of Quinone Monoimides and Conversion of Active Methylene Adducts to Benzofurans", Journal of the American Chemical Society, American Chemical Society, Feb. 1, 1956, pp. 658-663, vol. 78, No. 3.
V.M. Lyubchanskaya V M et al., "Quinoneimines in the Nenitzescu reaction", Russian Chemical Bulletin, Jul. 1, 2005, pp. 1690-1699, vol. 54, No. 7, Kluwer Academic Publishers-PLenum Publishers, NE.

* cited by examiner

*Primary Examiner* — T. Victor Oh
(74) *Attorney, Agent, or Firm* — Arent Fox LLP

(57) ABSTRACT

The present invention relates to a process for the preparation of 3-aroyl-5-aminobenzofuran derivatives useful as antiarrhythmic drugs which avoids the use of nitro intermediates.

14 Claims, No Drawings

PROCESS FOR THE PREPARATION OF 3-AROYL-5-AMINOBENZOFURAN DERIVATIVES

CROSS-REFERENCE TO RELATED APPLICATION

This application is a National Stage entry of International Application No. PCT/EP2011/069974, filed Nov. 11, 2011, which claims priority to European Application No. EP10191060.2, filed Nov. 12, 2010, the entire specifications, claims and drawings of which are incorporated herewith by reference.

FIELD OF THE INVENTION

The present invention relates to the field of organic chemistry, more specifically to a process for the preparation of 3-aroyl-5-aminobenzofuran derivatives useful as antiarrhythmic drugs.

BACKGROUND OF THE INVENTION

The 2-alkyl-3-aroylbenzofuran derivatives of Formula I,

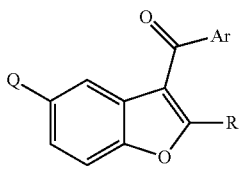

Formula I wherein R is lower alkyl and Ar is a substituted phenyl, are well known antiarrhythmic drugs. Two representative molecules, N-(2-butyl-3-(4-(3-(dibutylamino)propoxy)benzoyl)benzofuran-5-yl)methanesulfonamide—compound (1) and (2-butylbenzofuran-3-yl)(4-(2-(diethylamino) ethoxy)-3,5-diiodophenyl)methanone—compound (2) are currently active pharmaceutical ingredients on the market. The compound (1) is a recent enhancement versus compound (2) used for treatment of atrial fibrillation since decades.

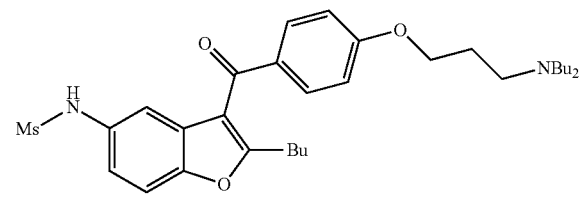

1

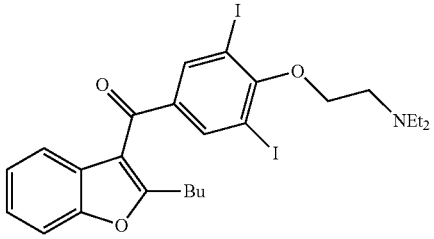

2

A basic approach to prepare 3-aroylbenzofuran derivatives includes Friedel-Crafts reaction of anisoyl chloride to benzofuran or 5-nitrobenzofuran ring, demethylation of methoxy group and side chain coupling (U.S. Pat. No. 3,248,401, EP 0425359, EP 0471609—Scheme 1). Harsh conditions of Friedel-Crafts reaction and demethylation are less suitable for routine industrial production. In a special case of preparation of 5-amino substituted derivatives at least two steps are needed for preparation of starting 2-butyl-5-nitrobenzofuran and two steps for conversion of nitro group, so the number of steps is increased to at least seven.

Scheme 1

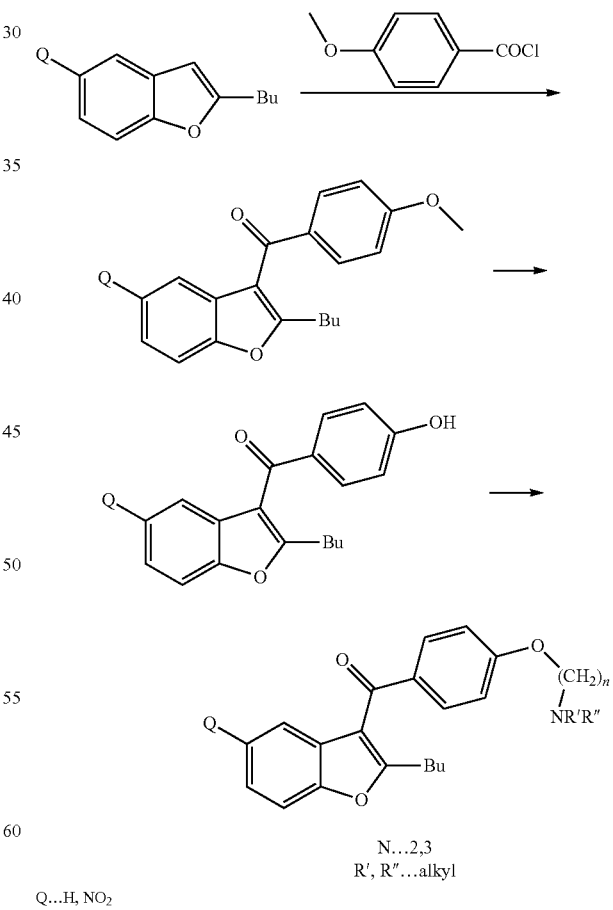

Q...H, NO$_2$

N...2,3
R', R"...alkyl

Similar, but more convergent approach is described in WO 02/048132 (Scheme 2).

Scheme 2
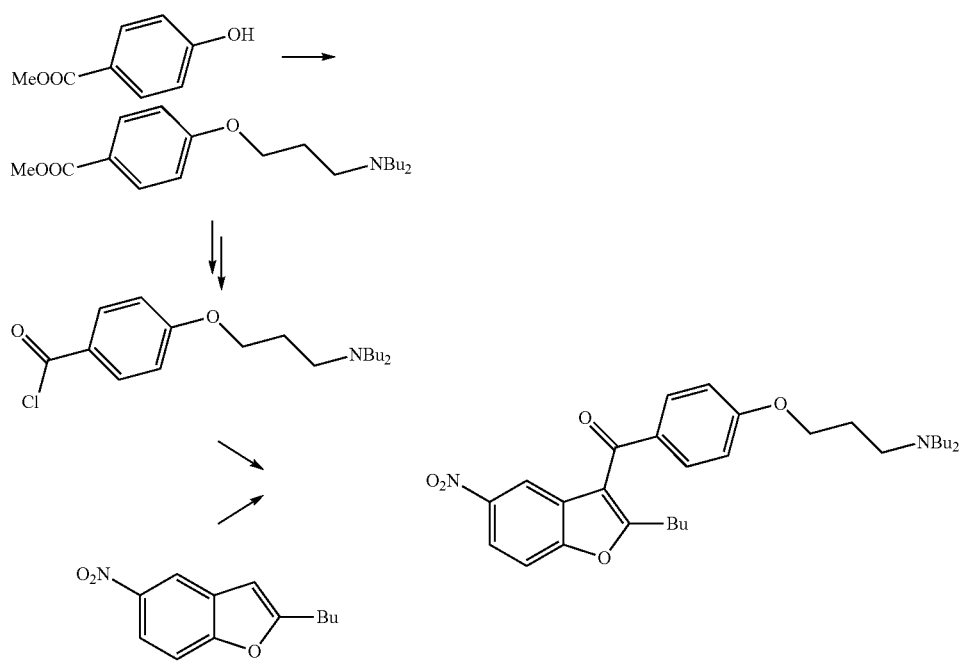
The patent application WO 05/066149 describes a reverse Friedel-Crafts reaction, but the main drawback of this approach is formation of byproducts arising from concurrent ortho substitution due to limited regioselectivity (Scheme 3).

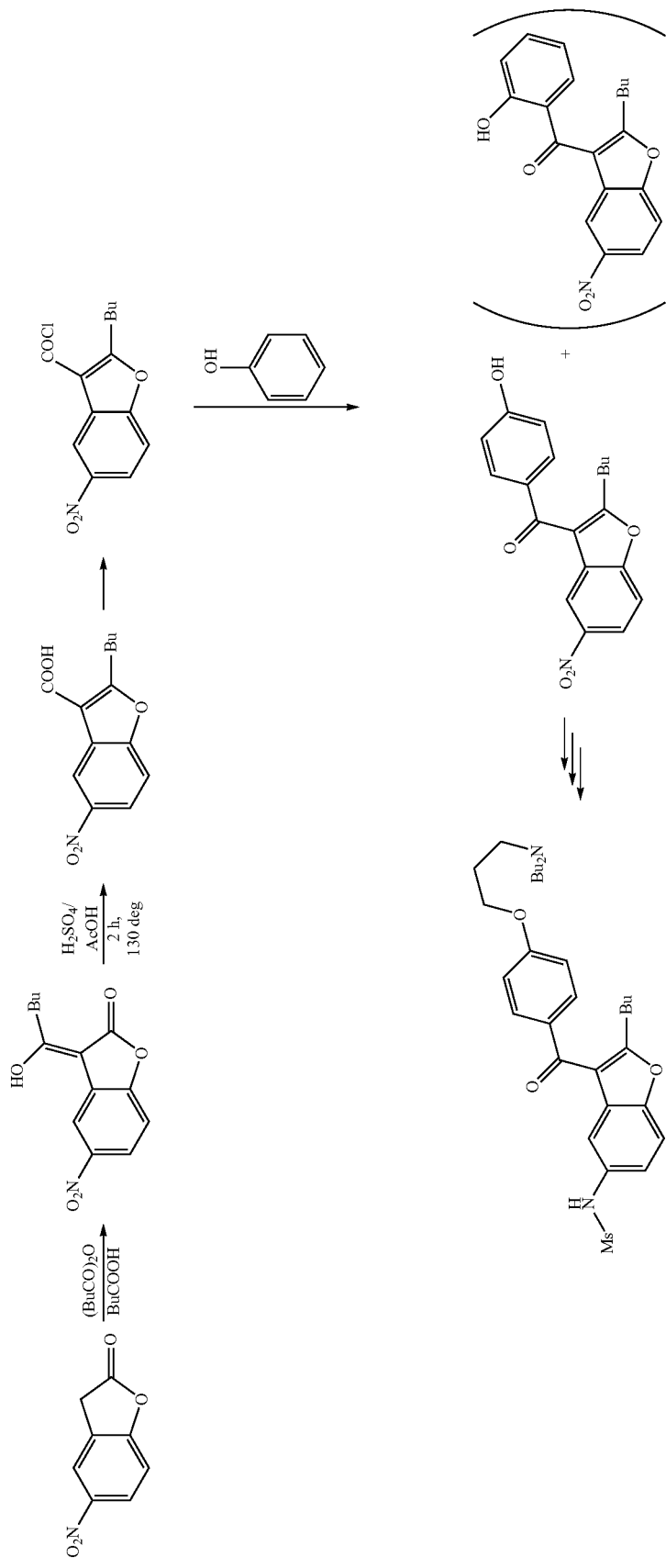

More recent approaches (WO 09/044,143, WO 10/038,029, WO 10/040,261) avoid Friedel-Crafts coupling and apply an oxa variation of the Fischer indole synthesis (Scheme 4)

The application WO 02/048132 describes a synthetic route wherein reduction of the nitro group is performed in earlier steps (Scheme 5), however, the preparation still needs the use of expensive catalysts and Friedel-Crafts conditions.

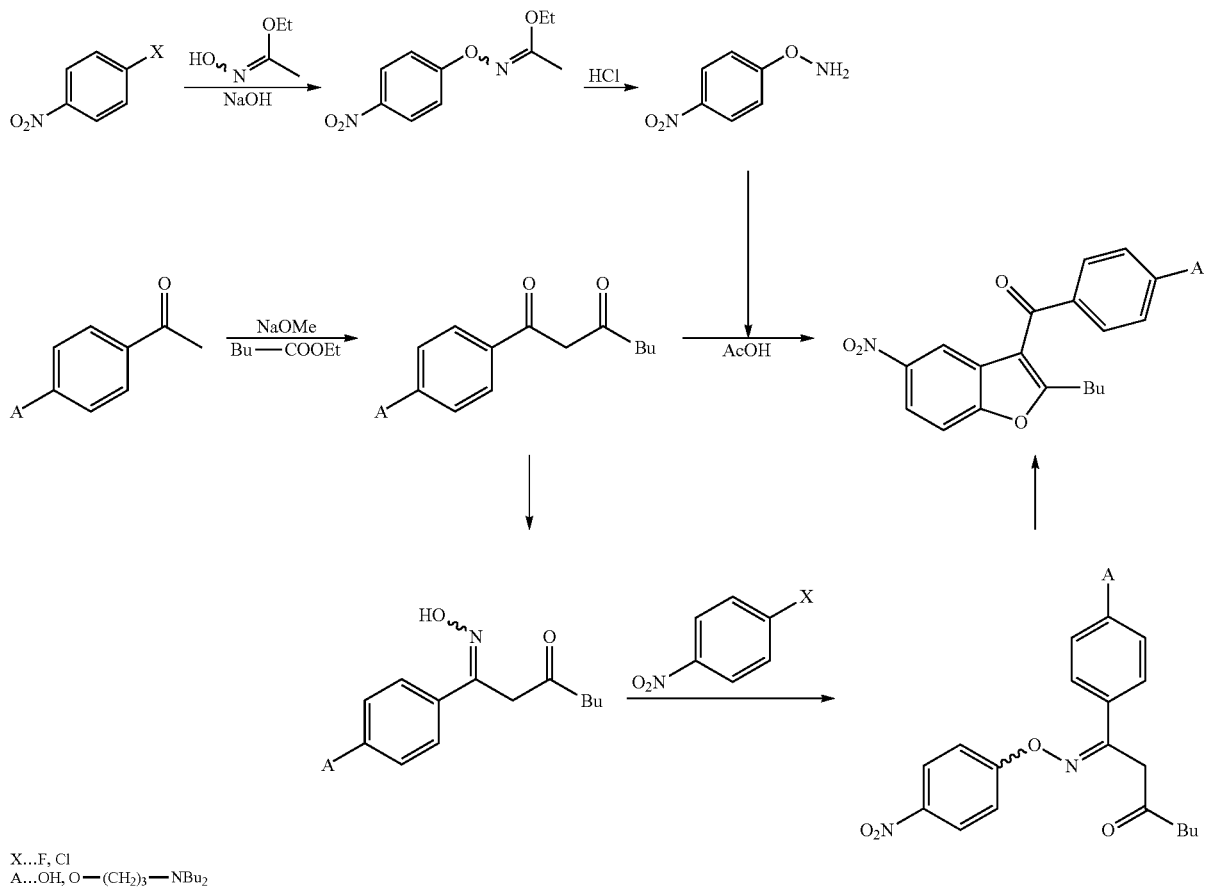

X...F, Cl
A...OH, O—(CH$_2$)$_3$—NBu$_2$

All of these synthetic procedures of 3-aroyl-5-aminobenzofuran derivatives started from nitro derivatives and the active molecule is finally converted to a pharmaceutically applicable form, which is often a pharmaceutically acceptable salt. It was surprisingly found that the preparation of salts of N-(2-butyl-3-(4-(3-(dibutylamino)propoxy)benzoyl) benzofuran-5-yl)methanesulfonamide from base is poorly reproducible, in most cases oils and foams were obtained. Time consuming additional efforts on purification of base have to be done in order to perform smooth preparation of solid N-(2-butyl-3-(4-(3-(dibutylamino)propoxy) benzoyl) benzofuran-5-yl)methanesulfonamide hydrochloride. Most of impurities originate in reduction of nitro group which proceeds via reactive nitroso, hydroxyamino and diazo intermediates that may produce several byproducts. It would be favorable to find better reduction conditions or to move the reduction step to earlier steps of the synthesis. The best solution would be to avoid nitro group all together. The nitro group is one of potential genotoxicity causing moieties in the molecule, so a handling of nitro compounds needs special measures in a production line.

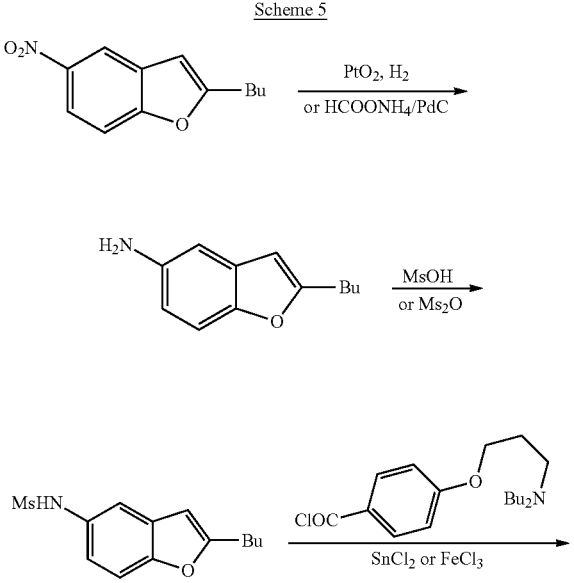

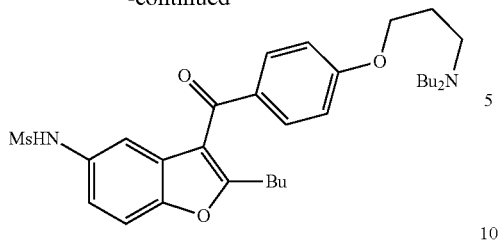

Another approach from the patent literature (WO 03/040120) avoids use of nitro intermediates but the procedure via alternative protection of amino group suffers from numerous steps.

There is still need for a short and efficient synthesis of 3-aroyl-5-aminobenzofuran derivatives. The invention satisfies this need.

DESCRIPTION OF THE INVENTION

In the following, the present invention will be described in more detail by preferred embodiments and examples while referring to the attached drawings, noting however, that these embodiments, examples and drawings are presented for illustrative purposes only and shall not limit the invention in any way.

1. A process for the preparation of 5-aminobenzofuran derivatives of Formula V or salts thereof

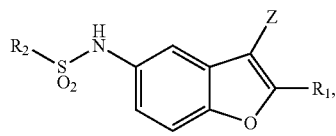

Formula V wherein
$R_1$ is selected from $C_1$-$C_8$-alkyl,
$R_2$ is selected from $C_1$-$C_8$-alkyl, fluorinated $C_1$-$C_8$-alkyl, phenyl, para substituted phenyl, and
Z is cyano or C(O)R, wherein
R is selected from hydrogen, hydroxy, $C_1$-$C_4$-alkoxy, benzyloxy or substituted benzyloxy, $NR^yR^z$ wherein $R^y$ and $R^z$ are the same or different and selected from hydrogen, $C_1$-$C_4$-alkyl, methoxy, or $R^y$, $R^z$ are fused to a link —$(CH_2)_m$—V—$(CH_2)_2$— wherein m an integer from 1-3, and —V— is —$CH_2$—, —O— or —NR'''— wherein R''' is hydrogen, methyl or ethyl,
or R represents a benzene ring having a halo substituent in none, one or both of the meta positions and having a fluoro, chloro, bromo, iodo, nitro, $C_1$-$C_8$-alkyl, substituted $C_1$-$C_8$-alkyl, hydroxy, $C_1$-$C_8$-alkoxy, substituted $C_1$-$C_8$-alkoxy, $C_1$-$C_8$-alkylamino or substituted $C_1$-$C_8$-alkylamino substituent in para position, the process comprising
a) treating a sulfonimidoquinone of Formula III

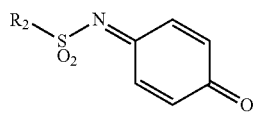

Formula III with a compound of Formula IV in any one of enaminic, enolic, ketonic or iminic tautomeric forms thereof,

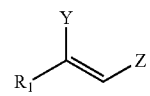

Formula IV wherein Y is selected from
hydroxy, $C_1$-$C_2$-alkoxy, phenoxy,
—$OSi(R^a)_3$ wherein $R^a$ is the same or different and selected from $C_1$-$C_4$-alkyl or phenyl,
—$OSO_2R^b$ wherein $R^b$ is selected from unsubstituted or fluorinated $C_1$-$C_4$-alkyl, or phenyl,
—$OP(O)(OR^c)_2$ wherein $R^c$ is selected from $C_1$-$C_4$-alkyl, or phenyl, or
di-$C_1$-$C_4$-alkylamino, pyrrolidino, piperidino, morpholino, and
Z is as defined above.

2. The process according to item 1 for the preparation of derivatives of 3-aroyl-5-aminobenzofuran derivatives of Formula I

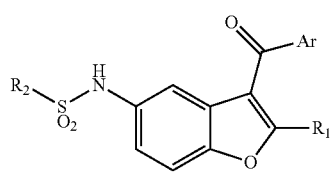

Formula I or pharmaceutical acceptable salts thereof,
wherein $R_1$ and $R_2$ are as defined in item 1 and the compound of Formula III is treated with the compound of Formula IV wherein Z is C(O)Ar and Ar is representing a benzene ring having a halo substituent in none, one or both of the meta positions and having a fluoro, chloro, bromo, iodo, nitro, $C_1$-$C_8$-alkyl, substituted $C_1$-$C_8$-alkyl, hydroxy, $C_1$-$C_8$-alkoxy, substituted $C_1$-$C_8$-alkoxy, $C_1$-$C_8$-alkylamino or substituted $C_1$-$C_8$-alkylamino substituent in para position.

3. The process according to item 1 for the preparation of derivatives of a compound of Formula II

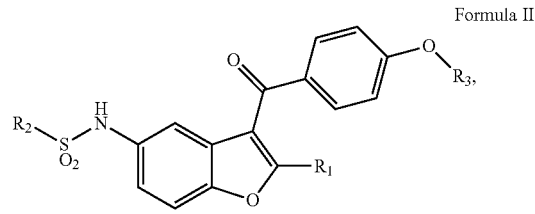

Formula II wherein $R_3$ is hydrogen, a phenol protected group or $(CH_2)_n NR'R''$, wherein n is an integer 2-6 and R', R'' are the same or different and selected from $C_1$-$C_6$-alkyl, benzyl, substituted benzyl or R', R'' are fused by —$(CH_2)_m$—V—$(CH_2)_2$— wherein m is an integer from 1-3, and —V— is —$CH_2$—, —O— or —NR'''— wherein R''' is hydrogen, methyl or ethyl, the process comprising a) treating the sulfonimidoquinone of Formula III

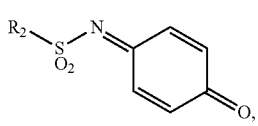
Formula III wherein $R_2$ is as defined in item 1,
with a compound of Formula IV in any one of enaminic, enolic, ketonic or iminic tautomeric forms thereof,

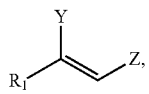
Formula IV wherein $R_1$ and Y are as defined in item 1 and
Z is a substituent defined by the structure

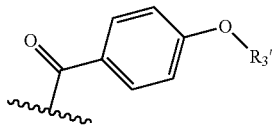

wherein $R_3'$ is hydrogen, a phenol protected group or $(CH_2)_n NR'R''$ wherein n is an integer 2-6 and R', R'' are the same or different and selected from $C_1$-$C_6$-alkyl, benzyl, substituted benzyl or are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl to give a compound of Formula II$^A$

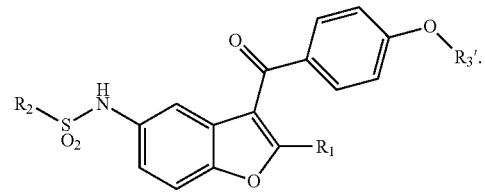
Formula II$^A$ b) optionally converting the compounds of Formula II$^A$ into compounds of Formula II in case $R_3$ is not $R_3'$.

4. The process according to item 3 for the preparation of the compound of Formula II comprising
a) treating the sulfonimidoquinone of Formula III

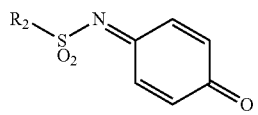
Formula III with a compound of Formula IX

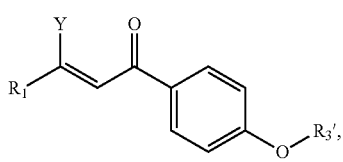
Formula IX wherein $R_1$, $R_2$, Y and $R_3'$ are as defined in item 3, to give the compound of Formula II$^A$

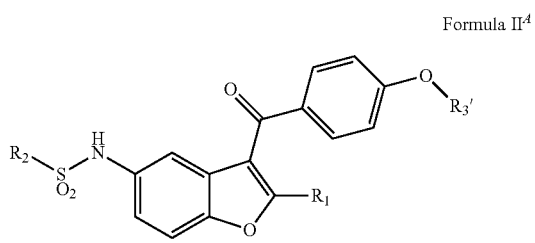
Formula II$^A$ b) converting the compounds of Formula II$^A$ into compounds of Formula II in case $R_3$ is not $R_3'$.

5. The process according to item 3, wherein the sulfonimidoquinone of Formula III

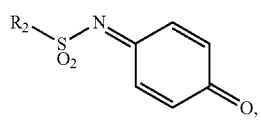
Formula III wherein $R_2$ is as defined in item 1
is treated with a compound of Formula IX$^C$

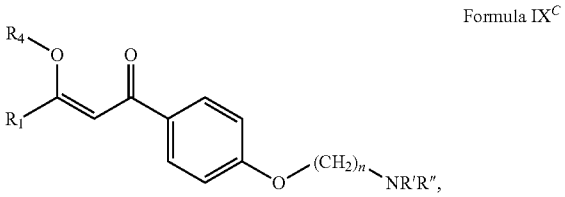
Formula IX$^C$ wherein $R_1$ is as defined in item 1, n is an integer from 2-6 and
$R_4$ is selected from
—Si$(R^a)_3$ wherein $R^a$ is the same or different and selected from $C_1$-$C_4$-alkyl or phenyl,
—$SO_2R^b$ wherein $R^b$ selected from unsubstituted or fluorinated $C_1$-$C_4$-alkyl, or phenyl,
—P(O)(OR$^c$)$_2$ wherein $R^c$ is selected from $C_1$-$C_4$-alkyl, or phenyl, and
R', R'' are the same or different and selected from $C_1$-$C_6$-alkyl, benzyl, substituted benzyl, or R', R'' are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl.

6. The process according to item 5, wherein the compound of Formula IX$^C$ is provided comprising
a) treating a compound of Formula VI

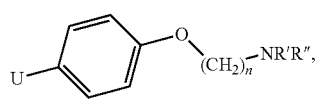
Formula VI wherein U is selected from acetyl and R', R'' are the same or different and selected from $C_1$-$C_6$-alkyl, benzyl, substituted benzyl, or are fused to —$(CH_2)_2$—NR'''—$(CH_2)_2$—, wherein R''' is hydrogen, methyl or ethyl, n is an integer from 2-6 with an ester of formula R₁—CO-A', wherein R₁ is selected from $C_1$-$C_8$-alkyl, and A' is $C_1$-$C_4$-alkoxy, $C_1$-$C_8$-acyloxy, halo or benzotriazolyloxy to give a compound of Formula XII

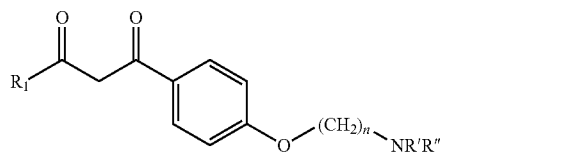

Formula XII b) subsequently treating the compound of Formula XII with a compound of formula $R_4X$ wherein $R_4$ is as defined in item 5 and X is halo.

7. The process according to item 3, wherein the sulfonimidoquinone of Formula III

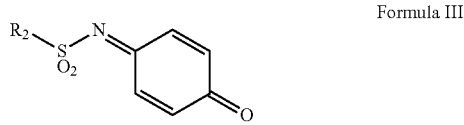

Formula III is treated with a compound of Formula $X^D$

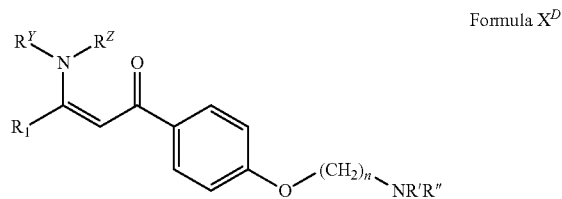

Formula $X^D$ wherein $R_1$ is as defined in item 1, n is an integer from 2-6 and $R^yR^z$ and R', R" are the same or different and selected from $C_1$-$C_6$-alkyl, benzyl, substituted benzyl or $R^y$, $R^z$ and R', R" respectively are fused to alkylene —(CH₂)ₘ— wherein m is integer 4-6, or R', R" are fused to a link —(CH₂)ₘ—V—(CH₂)₂— wherein m is an integer from 1-3, and —V— is —CH₂—, —O— or —NR'''— wherein R''' is hydrogen, methyl or ethyl.

8. The process according to item 7, wherein the compound of Formula $X^D$ is provided comprising a) treating the compound of Formula VI

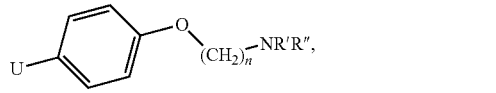

Formula VI wherein U, R', R" and n are as defined in item 6 with an amide of formula R₁—CO—NR^yR^z or with an activated form of an acetal of Formula XIII

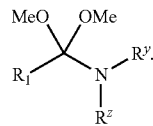

Formula XIII or with an ortho ester R₁C(ORᵒ)₃ in the presence of amine HNR^yR^z, wherein Rᵒ is selected from methyl or ethyl and R₁, R^y and R^z are as defined in item 7.

9. The process according to item 1, comprising a) treating the compound of Formula III with a compound of Formula IV^A

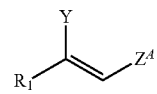

Formula IV^A wherein R₁, R₂, and Y are as defined in item 1 and wherein Z^A is cyano or C(O)R, wherein R is selected from hydrogen, hydroxyl, $C_1$-$C_4$-alkoxy, benzyloxy or substituted benzyloxy, NR^yR^z wherein R^y and R^z are the same or different and selected from hydrogen, $C_1$-$C_4$-alkyl, methoxy, or are fused by —(CH₂)ₘ—V—(CH₂)₂—, wherein m an integer from 1-3 and —V— is —CH₂—, —O— or —NR'''—, wherein R''' is hydrogen, methyl or ethyl, b) treating the compound obtained from step a) with a compound of Formula VI^A

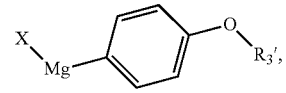

Formula VI^A wherein X represents chloro, bromo or iodo, and $R_3'$ is hydrogen, a phenol protecting group or (CH₂)ₘNR'R" wherein n is an integer 2-6 and R', R" are the same or different and selected from $C_1$-$C_6$-alkyl, benzyl, substituted benzyl or R', R" are fused to a link —(CH₂)ₘ—V—(CH₂)₂— wherein m is an integer from 1-3, and —V— is —CH₂—, —O— or —NR'''— wherein R''' is hydrogen, methyl or ethyl, c) optionally converting the compound obtained from step b) to a compound of Formula I.

10. The process according to item 9, wherein in step b) the compound of Formula IV^A

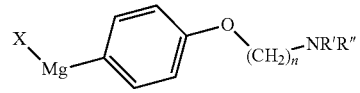

Formula IV^A is used, wherein X is halo, n is an integer 2-6 and R', R" are the same or different and selected from $C_1$-$C_6$-alkyl, benzyl, substituted benzyl or are fused to alkylene —(CH$_2$)$_m$—, wherein m is an integer 4-6, or R', R" are fused to a link —(CH$_2$)$_m$—, —V—(CH$_2$)$_2$— wherein m is an integer from 1-3, and —V— is —CH$_2$—, —O— or —NR'''—, wherein R''' is hydrogen, methyl or ethyl.

11. The process according to item 10, wherein the compound of Formula IV$^A$ is provided comprising treating the compound of Formula VI

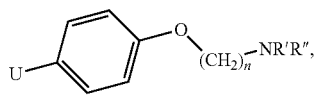

Formula VI wherein U, R', R" and n are as defined in item 6 with elemental magnesium or with R$^M$MgX wherein R$^M$ is methyl, ethyl or vinyl and X is halo.

12. The process according to item 1, comprising
a) treating the compound of Formula III with a compound of Formula IV$^A$

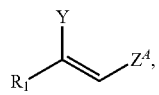

Formula IV$^A$ wherein R$_1$, R$_2$, and Y are as defined in item 1 and Z$^A$ is cyano or C(O)R, wherein R is selected from C$_1$-C$_4$-alkoxy, benzyloxy or substituted benzyloxy, NR$^y$R$^z$ wherein R$^y$ and R$^z$ are the same or different and selected from hydrogen, C$_1$-C$_4$-alkyl, methoxy, or are fused by —(CH$_2$)$_m$—V—(CH$_2$)$_2$—, wherein m an integer from 1-3 and —V— is —CH$_2$—, —O— or —NR'''—, wherein R''' is hydrogen, methyl or ethyl, b) converting the compound resulting from step a) into a compound of Formula VII

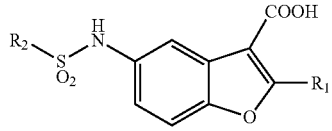

Formula VII by oxidation, hydrolysis or hydrogenolysis c) optionally converting the compound of Formula VII to a compound of Formula VIII

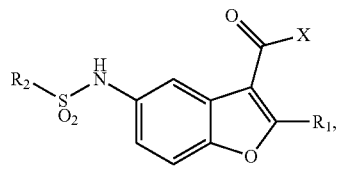

Formula VIII by treating the compound of Formula VII with reactive sulfur, phosphorus, and acyl halogenides, wherein X is selected from halo or acyl, d) treating the compound of Formula VIII with a compound of Formula VI$^B$

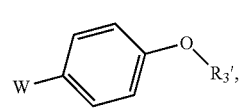

Formula VI$^B$ wherein W represents hydrogen, chloro, bromo or iodo and R$_3$' is hydrogen, a phenol protecting group or (CH$_2$)$_n$NR'R" wherein n is an integer 2-6 and R', R" are the same or different and selected from C$_1$-C$_6$-alkyl, benzyl, substituted benzyl or R', R" are fused to a link —(CH$_2$)$_m$—V—(CH$_2$)$_2$—, wherein m is an integer from 1-3, and —V— is —CH$_2$—, —O— or —NR'''—, wherein R''' is hydrogen, methyl or ethyl.

13. The process according to item 12, wherein the compound of Formula VI$^B$ with W=Br is converted to an organo-metal intermediate comprising organomagnesium, organoaluminium intermediate, or organoboron intermediate prior to the reaction with the compound of Formula VIII.

14. The process according to item 12, wherein step d) with the compound of Formula VI$^B$ and W=H is performed under Friedel-Crafts electrophilic substitution conditions using Friedel-Crafts catalysts comprising aluminium trichloride, tin tetrachloride, and iron trichloride.

15. The process according to item 3, wherein the compound of Formula II$^A$

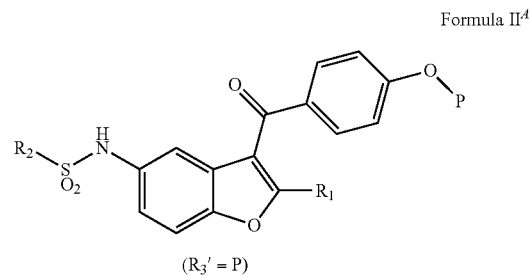

Formula II$^A$ (R$_3$' = P)

wherein R$_1$ and R$_2$ are as defined in item 3 and R$_3$' is a phenol protecting group P selected from methyl, arylmethyl, C$_1$-C$_4$-alkoxymethyl, unsubstituted or substituted C$_1$-C$_8$-acyl, C$_1$-C$_8$-alkylsulfonyl, fluorinated C$_1$-C$_8$-alkylsulfonyl, benzenesulfonyl, para substituted benzenesulfonyl, camphor-10-sulfonyl, or OSi(R$^a$)$_3$ wherein R$^a$ is the same or different and selected from C$_1$-C$_4$-alkyl or phenyl, is transformed to the compound of Formula II

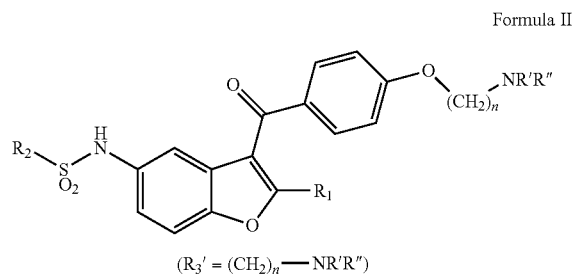

Formula II (R$_3$' = (CH$_2$)$_n$—NR'R")

wherein R$_3$ is selected from (CH$_2$)$_n$NR'R" wherein n is an integer 2-6 and R', R" are the same or different and selected from $C_1$-$C_6$-alkyl, benzyl, substituted benzyl or are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, by a) deprotecting with corresponding reagents to give a phenol of Formula II$^A$ ($R_3'$=H)

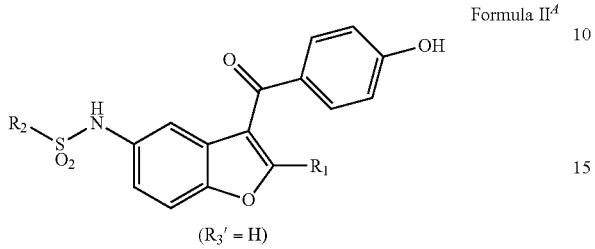

Formula II$^A$ ($R_3'$ = H)

b) substituting the phenolic hydroxyl group by the compound of formula L-$(CH_2)_n$-A, wherein L is a leaving group, selected from halo or $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, and A is another leaving group L' or NR'R'' wherein n is an integer 2-6 and R', R'' are the same or different and selected from $C_1$-$C_6$-alkyl, benzyl, substituted benzyl or are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, wherein L and L' represent leaving groups in reactions of nucleophilic substitution and are the same or different, to give the compound of Formula II$^A$

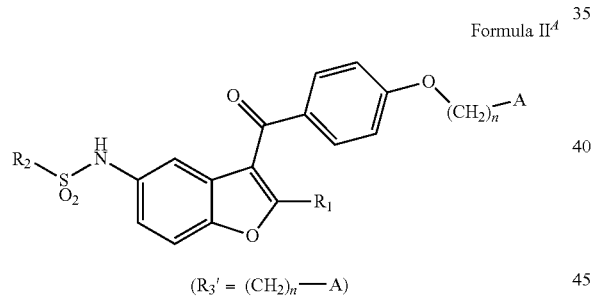

Formula II$^A$ ($R_3'$ = $(CH_2)_n$—A)

c) optionally if A is the leaving group L' further treating with the amine HNR'R'' wherein n is an integer 2-6 and R', R'' are the same or different and selected from $C_1$-$C_6$-alkyl, benzyl, substituted benzyl or R', R'' are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl.

16. The process according to item 3 for the preparation of derivatives of 3-aroyl-5-aminobenzofuran derivatives of Formula II

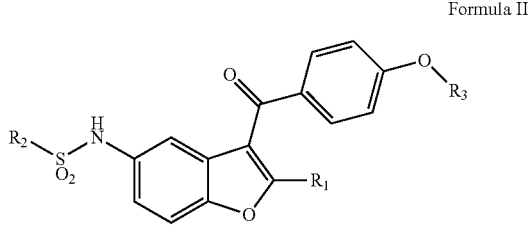

Formula II or pharmaceutical acceptable salts thereof, wherein $R_1$ is selected from n-butyl, $R_2$ from methyl and $R_3$ from 3-(dibutylamino)-1-propyl 17. A use of the compound of Formula III

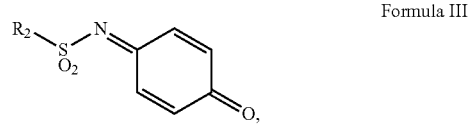

Formula III wherein $R_2$ is selected from $C_1$-$C_8$-alkyl, fluorinated $C_1$-$C_8$-alkyl, phenyl, para substituted phenyl for the synthesis of dronedarone.

18. A process for the preparation of dronedarone or pharmaceutically acceptable salt thereof comprising the steps of:

a) carrying out a process as defined in any one of items 1 to 16 and b) optionally, in case the compound obtained from step a) is not already dronedarone or pharmaceutically acceptable salts thereof, subjecting the obtained compound to further synthesis steps to yield dronedarone or pharmaceutically acceptable salts thereof.

19. A process for the preparation of a pharmaceutical composition comprising dronedarone as active ingredient, comprising the steps of:

a) preparing dronedarone or pharmaceutically acceptable salts thereof according to the process as defined in any one of items 1 to 16, and b) admixing the thus prepared dronedarone or pharmaceutically acceptable salt thereof with at least one pharmaceutically acceptable excipient.

20. The process according to item 19, wherein the excipient in step b) is selected from the group consisting of binders, diluents, disintegrating agents, stabilizing agents, preservatives, lubricants, fragrances, flavoring agents, sweeteners and other excipients known in the field of the pharmaceutical technology.

21. 5-Aminobenzofuran derivatives of Formula V or salts thereof as defined in any one of items 1 to 3.

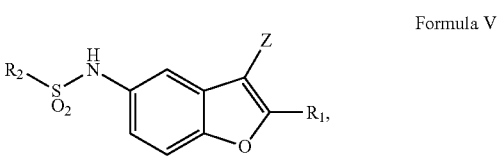

Formula V

Any one of Compounds I, II, II$^A$, III, IV, IV$^A$, VI, VI$^A$, VI$^B$, XII, IX$^C$ as defined in the items above is also a specific embodiment of the present invention. Any one of compounds XIII, IV$^E$, IV$^C$, X$^D$ as defined hereinafter is also a specific embodiment of the present invention.

The term "alkyl" as used herein, if not stated otherwise with respect to particular embodiments, includes reference to a straight or branched chain alkyl moiety having from 1 to 8 carbon atoms. This term includes methyl, ethyl, propyl (n-propyl or isopropyl), butyl (n-butyl, sec-butyl or tert-butyl), pentyl, hexyl and the like. In particular, alkyl may have 1, 2, 3 or 4 carbon atoms. The abbreviation Bu in structure formulas if not stated otherwise with respect to particular embodiments, represents n-butyl.

The term "alkylene" as used herein, if not stated otherwise with respect to particular embodiments, include reference to a straight or branched aliphatic chain of 2, 3, 4, 5 or 6 carbon atoms which is attached to a main structure by two bonds from different carbon atoms of the chain. In particular, this term includes methylene, ethylene, 1,2-propylene, 1,3-propylene, 2,3-butylene, 2-methyl-2,3-butylene, 2,3-dimethyl-2,3-butylene, 1,2-cyclohexylidene and the like.

The term "alkoxy" as used herein, if not stated otherwise with respect to particular embodiments, include alkyl substituted hydroxyl group, wherein alkyl is straight or branched chain and comprises 1 to 8 carbon atoms. In certain embodiments, alkoxy has 1, 2, 3 or 4 carbon atoms. This term includes methoxy, ethoxy, propoxy, isopropoxy, butoxy, tert-butoxy, pentoxy, hexoxy and the like.

The term "aryl" as used herein, if not stated otherwise with respect to particular embodiments, includes reference to an aromatic ring system comprising 6, 7, 8, 9, 10, 11, 12, 13, 14, 15 or 16 ring carbon atoms, which may be substituted. Aryl is often phenyl but may be a polycyclic ring system, having two or more rings, at least one of which is aromatic. This term includes phenyl, naphthyl, fluorenyl, azulenyl, indenyl, anthryl and the like.

The term halo as used herein, if not stated otherwise with respect to particular embodiments, includes reference to chloro, bromo, iodo, and does not include fluoro.

The term "acyl" or "acyl substituted" as used herein means a group originated from an aliphatic or aromatic carboxylic acid, preferably selected from $C_1$-$C_{20}$-alkanoic, substituted $C_1$-$C_{20}$-alkanoic, arylcarboxylic, substituted arylcarboxylic wherein the corresponding alkyl, substituted alkyl, aryl or substituted alkyl is attached to the main structure via intermediate carbonyl (CO) group. For a special case of arylcarboxylic and substituted arylcarboxylic originated radical the term "aroyl" is used.

The term "sulfonyl" or "sulfonyl substituted" as used herein means a group originated from a sulfonic acid, preferably selected from alkylsulfonic, fluoro substituted alkylsulfonic, arylsulfonic, camphoryl sulfonic acids wherein the corresponding alkyl, fluoro substituted alkyl, aryl or camphoryl is attached to the main structure via intermediate sulfonyl ($SO_2$) group. For a special case of sulfonyl group coupled to iminic nitrogen group a term "sulfonimido" is used.

The term "substituted" as used herein in reference to a structure/moiety/group, if not defined specifically in respective contexts means that one or more, especially up to 5, more especially 1, 2 or 3, of the hydrogen atoms in said structure/moiety/group are replaced independently of each other by the corresponding number of substituents known to a person skilled in the art. Typical substituents include, without being limited to halogen, trifluoromethyl, cyano, nitro, oxo, NR', —OR', —C(O)R', —C(O)OR', —OC(O)R', —S(O)R', N(R')R", C(O)N(R')R", —SO$_2$N(R')R' and R''', wherein each of R', R" and R''' are selected from the group consisting of $C_1$-$C_6$ alkyl, $C_1$-$C_6$ alkoxy, —(CH$_2$)$_m$-heterocyclyl (m being 1, 2, 4 or 4) and each R' and R" may be optionally and independently further substituted with one or more of hydrogen, halogen, cyano, amino, hydroxy, $C_1$-$C_6$ alkyl and $C_1$-$C_6$ alkoxy. Specific substituents in particular include halogen such as fluoro, chloro and/or bromo, hydroxy, amino, $C_1$-$C_6$ alkyl and $C_1$-$C_6$ alkoxy, and halogenated $C_1$-$C_6$ alkyl and $C_1$-$C_6$ alkoxy such as trifluoromethyl. It will be understood that substituents are at positions where they are chemically possible, it being known or evident to the person skilled in the art to decide (either experimentally or theoretically) without inappropriate effort whether a particular substitution is possible. For example, substituents which may be unstable or may affect reactions disclosed herein may be omitted, at least at the relevant stage of intermediate compound or of the affected reaction. In particular the term substituted may mean substituted by halo, hydroxy, $C_1$-$C_6$-alkoxy, acyloxy, $C_1$-$C_4$-alkylsulfonyloxy or fluorinated $C_1$-$C_4$-alkylsulfonyloxy or substituted amino characterized by NR'R" wherein n is an integer 2-6 and R', R" are the same or different and selected from hydrogen, $C_1$-$C_6$-alkyl, benzyl, substituted benzyl, or R', R" are fused to a link —(CH$_2$)$_m$—V—(CH$_2$)$_2$— wherein m is an integer from 1-3, and —V— is —CH$_2$—, —O— or NR'''—, wherein R''' is hydrogen, methyl or ethyl.

The term "base substance" used herein according to preferred embodiments can be any base known and typically used in organic synthesis. The base can include, without being limited to amides, hydrides, hydroxides, amidines, guanidines or amines. The preferred base is selected from hydroxides, ammonia, tertiary amines, and inorganic basic salts such as acetates, carbonates or phosphates.

The term "Broensted acid" represents a chemical substance or ion that is able to lose, or "donate" a proton and as used herein, if not stated otherwise with respect to particular embodiments, it is selected from inorganic (mineral) acids, such as hydrohalic acids, sulfuric acids, phosphoric acids, perchloric acid, from organic carboxylic acids, organic sulfonic acids, organic phosphonic acids, ammonium or azinium salts.

The term "Lewis acid" represents a chemical substance that can accept a pair of electrons and as used herein, if not stated otherwise with respect to particular embodiments, it is selected from compounds of transition metals or elements of column III of periodic table, preferably selected from anhydrous aluminium, iron, tin, zinc compounds, or electron poor organic compounds such as carbonium cations, preferably trityl cation.

The term "phenol protecting group" as used herein in reference to a structure/moiety/group means a group temporarily substituting phenolic hydroxy group, inert in conditions of reactions of the invention and easily removable after critical conversion not affecting the sulfonamido group and is not limitedly selected from methyl, arylmethyl, $C_1$-$C_4$-alkoxymethyl, unsubstituted or substituted by $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, or trisubstituted silyl, defined as Si(R$^a$)$_3$ wherein R$^a$ is the same or different and selected from $C_1$-$C_4$-alkyl or phenyl.

The reactions of imidoquinones in general are described in literature only in few papers (J. Am. Chem. Soc. 73, 1145 (1951); Chemistry Lett., 1987, 2169) with limited examples comprising less complex molecules. Particularly the use of imidoquinones for the synthesis of 3-aroyl-5-aminobenzofurans has not been clearly explained. In Russ. Chem. Bull. Int. Ed. 54, 1690 (2005), simple 3-benzoyl furans are prepared from N-aryl substituted 3-aminocrotonates, but in some conditions the condensation leads to indoles, not to benzofurans, so the regioselectivity cannot be predicted for 3-amino-2-alkenoates in general. In J. Am. Chem. Soc. 73, 1145 (1951), the regioselectivity is confirmed for condensation of imidoquinones with ketoesters. The only example in this publication, which applies diketones, describes a condensation of acetylacetone, which is symmetrical and therefore not questionable for regioselectivity on the positions 2 and 3 of benzofurans.

According to the embodiment of the present invention the preparation of 3-aroyl-5-aminobenzofuran derivatives of Formula I:

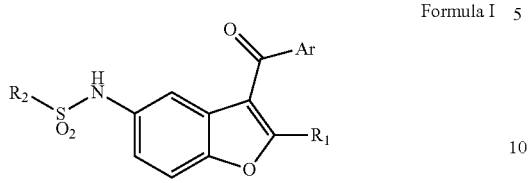

Formula I wherein $R_1$ is selected from $C_1$-$C_8$-alkyl, $R_2$ is selected from $C_1$-$C_8$-alkyl, fluorinated $C_1$-$C_8$-alkyl, phenyl, para substituted phenyl, and Ar represents a benzene ring having a halo substituent in none, one or both of the meta positions and having a fluoro, chloro, bromo, iodo, nitro, $C_1$-$C_8$-alkyl, substituted $C_1$-$C_8$-alkyl, hydroxy, $C_1$-$C_8$-alkoxy, substituted $C_1$-$C_8$-alkoxy, $C_1$-$C_8$-alkylamino or substituted $C_1$-$C_8$-alkylamino substituent in para position, wherein the term substituted as referred for substituents in Ar may mean substituted by halo, hydroxy, $C_1$-$C_6$-alkoxy, acyloxy, $C_1$-$C_4$-alkylsulfonyloxy or fluorinated $C_1$-$C_4$-alkylsulfonyloxy or substituted amino characterized by NR'R" wherein n is an integer 2-6 and R', R" are the same or different and selected from hydrogen, $C_1$-$C_6$-alkyl, benzyl, substituted benzyl or R', R" are fused to a link —$(CH_2)_m$—V—$(CH_2)_2$— wherein m is an integer from 1-3, and —V— is —$CH_2$—, —O— or —NR'"— wherein R'" is hydrogen, methyl or ethyl, optionally in the form of pharmaceutically acceptable salts, is performed by a) treating of sulfonimidoquinone of Formula III

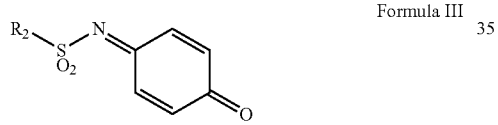

Formula III wherein $R_2$ is selected from $C_1$-$C_8$-alkyl, fluorinated $C_1$-$C_8$-alkyl, phenyl, para substituted phenyl, with a compound of the Formula IV comprising all enaminic, enolic, ketonic and iminic tautomeric forms thereof,

Formula IV wherein $R_1$ is selected from $C_1$-$C_8$-alkyl,

Y is selected from hydroxy, $C_1$-$C_2$-alkoxy, phenoxy,
—OSi($R^a$)$_3$ wherein $R^a$ is the same or different and selected from $C_1$-$C_4$-alkyl or phenyl,
—OSO$_2$$R^b$ wherein $R^b$ selected from unsubstituted or fluorinated $C_1$-$C_4$-alkyl, or phenyl, —OP(O)(O$R^c$)$_2$ wherein $R^c$ is selected from $C_1$-$C_4$-alkyl, or phenyl, or
di-$C_1$-$C_4$-alkylamino, pyrrolidino, piperidino, morpholino, and Z is selected from cyano or
C(O)R wherein R is selected from hydrogen, hydroxy, $C_1$-$C_4$-alkoxy, benzyloxy or substituted benzyloxy, NR$^y$R$^z$ wherein R$^y$ and R$^z$ are the same or different and selected from hydrogen, $C_1$-$C_4$-alkyl, methoxy, or R$^y$, R$^z$ are fused to a link —$(CH_2)_m$—V—$(CH_2)_2$— wherein m an integer from 1-3, and —V— is —$CH_2$—, —O— or —NR'"— wherein R'" is hydrogen, methyl or ethyl, or R represents a benzene ring having a halo substituent in none, one or both of the meta positions and having a fluoro, chloro, bromo, iodo, nitro, $C_1$-$C_8$-alkyl, substituted $C_1$-$C_8$-alkyl, hydroxy, $C_1$-$C_8$-alkoxy, substituted $C_1$-$C_8$-alkoxy, $C_1$-$C_8$-alkylamino or substituted $C_1$-$C_8$-alkylamino substituent in para position, wherein the term substituted as referred for substituents in Ar may mean substituted by halo, hydroxy, $C_1$-$C_6$-alkoxy, acyloxy, $C_1$-$C_4$-alkylsulfonyloxy or fluorinated $C_1$-$C_4$-alkylsulfonyloxy or substituted amino characterized by NR'R" wherein n is an integer 2-6 and R', R" are the same or different and selected from hydrogen, $C_1$-$C_6$-alkyl, benzyl, substituted benzyl or R', R" are fused to a link —$(CH_2)_m$—V—$(CH_2)_2$— wherein m is an integer from 1-3, and —V— is —$CH_2$—, —O— or —NR'"— wherein R'" is hydrogen, methyl or ethyl, to form the compound of Formula V

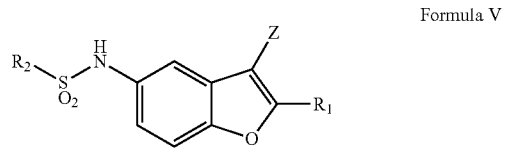

Formula V wherein $R_1$, $R_2$ and Z are the same as in Formula III and IV, b) converting the compound of Formula V to the compound of Formula I, proviso if the Formula I represents the same structure as Formula V c) optionally converting the compound of Formula I into the pharmaceutically acceptable salt.

According to the embodiment of the present invention the preparation of 3-aroyl-5-aminobenzofuran derivatives of Formula II:

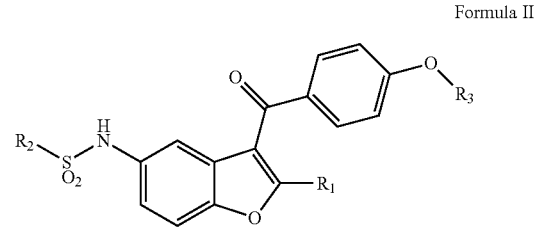

Formula II wherein $R_1$ is selected from $C_1$-$C_8$-alkyl, $R_2$ is selected from $C_1$-$C_8$-alkyl, fluorinated $C_1$-$C_8$-alkyl, phenyl, para substituted phenyl, and $R_3$ is hydrogen, a phenol protecting group or $(CH_2)_n$NR'R" wherein n is an integer 2-6 and R', R" are the same or different and selected from $C_1$-$C_6$-alkyl, benzyl, substituted benzyl or R', R" are fused to a link —$(CH_2)_m$—V—$(CH_2)_2$— wherein m is an integer from 1-3, and —V— is —$CH_2$—, —O— or —NR'"— wherein R'" is hydrogen, methyl or ethyl, optionally in the form of pharmaceutically acceptable salts, is performed by a) treating the sulfonimidoquinone of Formula III

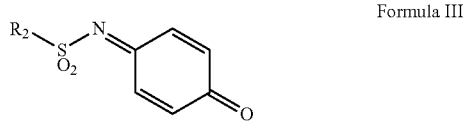

Formula III wherein $R_2$ is selected from $C_1$-$C_8$-alkyl, fluorinated $C_1$-$C_8$-alkyl, phenyl, para substituted phenyl,
with a compound of the Formula IV comprising all enaminic, enolic, ketonic and iminic tautomeric forms thereof,

Formula IV wherein $R_1$ is selected from $C_1$-$C_8$-alkyl,
Y is selected from
hydroxy, $C_1$-$C_2$-alkoxy, phenoxy,
—OSi($R^a$)$_3$ wherein $R^a$ is the same or different and selected from $C_1$-$C_4$-alkyl or phenyl,
—OSO$_2$R$^b$ wherein R$^b$ selected from unsubstituted or fluorinated $C_1$-$C_4$-alkyl, or phenyl, —OP(O)(OR$^c$)$_2$ wherein $R^c$ is selected from $C_1$-$C_4$-alkyl, or phenyl, or
di-$C_1$-$C_4$-alkylamino, pyrrolidino, piperidino, morpholino, and
Z is selected from cyano or
C(O)R wherein R is selected from hydrogen, hydroxy, $C_1$-$C_4$-alkoxy, benzyloxy or substituted benzyloxy, NR$^y$R$^z$ wherein R$^y$ and R$^z$ are the same or different and selected from hydrogen, $C_1$-$C_4$-alkyl, methoxy, or R$^y$, R$^z$ are fused to a link —(CH$_2$)$_m$—V—(CH$_2$)$_2$— wherein m an integer from 1-3, and —V— is —CH$_2$—, —O— or —NR'''— wherein R''' is hydrogen, methyl or ethyl, or
a substituent defined by the structure

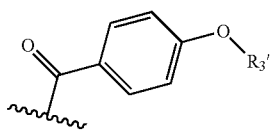

wherein $R_3$' is hydrogen, a phenol protected group or (CH$_2$)$_n$NR'R'' wherein n is an integer 2-6 and R', R'' are the same or different and selected from $C_1$-$C_8$-alkyl, benzyl, substituted benzyl or R', R'' are fused to a link —(CH$_2$)$_m$—V—(CH$_2$)$_2$— wherein m is an integer from 1-3, and —V— is —CH$_2$—, —O— or —NR'''— wherein R''' is hydrogen, methyl or ethyl, to form the compound of Formula V

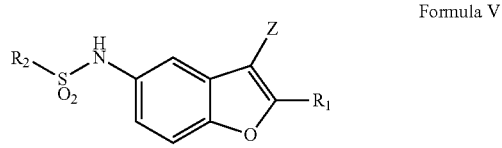

Formula V wherein $R_1$, $R_2$ and Z are the same as in Formula III and IV,
b) converting the compound of Formula V to the compound of Formula II, proviso if the Formula II represents the same structure as Formula V c) optionally converting the compound of Formula II into the pharmaceutically acceptable salt.

In a special but not limited case $R_1$ is selected from n-butyl, $R_2$ from methyl and $R_3$ from 3-(dibutylamino)-1-propyl.

According to a special embodiment A of the present invention the preparation of 3-aroyl-5-aminobenzofuran derivatives of Formula II:

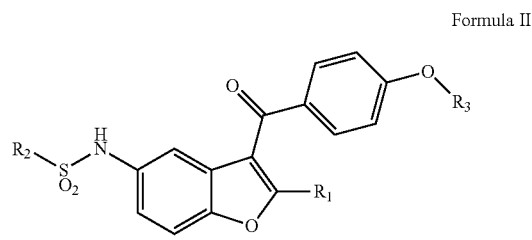

Formula II wherein $R_1$ is selected from $C_1$-$C_8$-alkyl, $R_2$ is selected from $C_1$-$C_8$-alkyl, fluorinated $C_1$-$C_8$-alkyl, phenyl, para substituted phenyl, and $R_3$ is hydrogen, a phenol protecting group or (CH$_2$)$_n$NR'R'' wherein n is an integer 2-6 and R', R'' are the same or different and selected from $C_1$-$C_6$-alkyl, benzyl, substituted benzyl or R', R'' are fused to a link —(CH$_2$)$_m$—V—(CH$_2$)$_2$— wherein m is an integer from 1-3, and —V— is —CH$_2$—, —O— or —NR'''— wherein R''' is hydrogen, methyl or ethyl, optionally in the form of pharmaceutically acceptable salts, is performed by
a) treating the sulfonimidoquinone of Formula III

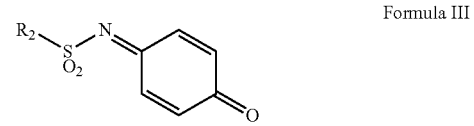

Formula III wherein $R_2$ is selected from $C_1$-$C_8$-alkyl, fluorinated $C_1$-$C_8$-alkyl, phenyl, para substituted phenyl,
with a compound of Formula IV$^A$:

Formula IV$^A$ wherein $R_1$ is selected from $C_1$-$C_8$-alkyl,
Y is selected from
hydroxy, $C_1$-$C_2$-alkoxy, phenoxy,
—OSi($R^a$)$_3$ wherein $R^a$ is the same or different and selected from $C_1$-$C_4$-alkyl or phenyl,
—OSO$_2$R$^b$ wherein R$^b$ selected from unsubstituted or fluorinated $C_1$-$C_4$-alkyl, or phenyl, —OP(O)(OR$^c$)$_2$ wherein $R^c$ is selected from $C_1$-$C_4$-alkyl, or phenyl, or
di-$C_1$-$C_4$-alkylamino, pyrrolidino, piperidino, morpholino, and
Z$^A$ is selected from cyano or
C(O)R wherein R is selected from hydroxy, $C_1$-$C_4$-alkoxy, benzyloxy or substituted benzyloxy, NR$^y$R$^z$ wherein R$^y$ and R$^z$ are the same or different and selected from hydrogen, $C_1$-$C_4$-alkyl, methoxy, or R$^y$, R$^z$ are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, to form the compound of Formula V$^A$

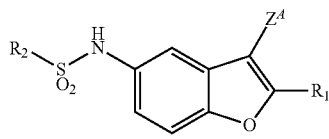

Formula V$^A$ wherein R$_1$, R$_2$ and Z$^A$ are the same as in Formula III and IV$^A$, b) converting the compound of Formula V$^A$ to the compound of Formula II, by
  i) treating the compound of Formula V$^A$ with Formula VI$^A$

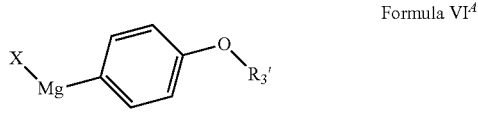

Formula VI$^A$ wherein X represents chloro, bromo or iodo, and R$_3$' is hydrogen, a phenol protecting group or (CH$_2$)$_n$NR'R" wherein n is an integer 2-6 and R', R" are the same or different and selected from C$_1$-C$_6$-alkyl, benzyl, substituted benzyl or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, to a compound of Formula II$^A$

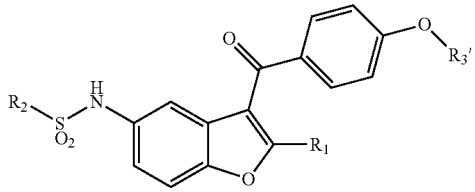

Formula II$^A$ wherein R$_1$, R$_2$ and R$_3$' are the same as in Formula III and VI$^A$, optionally in the presence of a catalyst, selected from a transition metal, ii) converting the compound of Formula II$^A$ to the compound of Formula II, proviso if R$_3$ is the same as R$_3$' c) optionally converting the compound of Formula II into the pharmaceutically acceptable salt.

In a special but not limited case R$_1$ is selected from n-butyl, R$_2$ from methyl and R$_3$ from 3-(dibutylamino)-1-propyl.

According to a special embodiment B of the present invention the preparation of 3-aroyl-5-aminobenzofuran derivatives of Formula II:

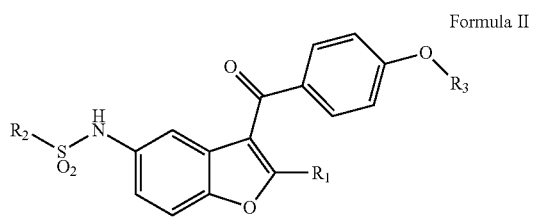

Formula II wherein R$_1$ is selected from C$_1$-C$_8$-alkyl, R$_2$ is selected from C$_1$-C$_8$-alkyl, fluorinated C$_1$-C$_8$-alkyl, phenyl, para substituted phenyl, and R$_3$ is hydrogen, a phenol protecting group or (CH$_2$)$_n$NR'R" wherein n is an integer 2-6 and R', R" are the same or different and selected from C$_1$-C$_6$-alkyl, benzyl, substituted benzyl or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, optionally in the form of pharmaceutically acceptable salts, is performed by c) treating the sulfonimidoquinone of Formula III

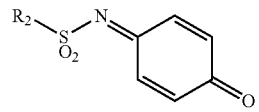

Formula III wherein R$_2$ is selected from C$_1$-C$_8$-alkyl, fluorinated C$_1$-C$_8$-alkyl, phenyl, para substituted phenyl, with a compound of Formula IV$^A$:

Formula IV$^A$ wherein R$_1$ is selected from C$_1$-C$_8$-alkyl,

Y is selected from hydroxy, C$_1$-C$_2$-alkoxy, phenoxy,

—OSi(R$^a$)$_3$ wherein R$^a$ is the same or different and selected from C$_1$-C$_4$-alkyl or phenyl, —OSO$_2$R$^b$ wherein R$^b$ selected from unsubstituted or fluorinated C$_1$-C$_4$-alkyl, or phenyl, —OP(O)(OR$^c$)$_2$ wherein R$^c$ is selected from C$_1$-C$_4$-alkyl, or phenyl, or di-C$_1$-C$_4$-alkylamino, pyrrolidino, piperidino, morpholino, and Z$^A$ is selected from cyano or C(O)R wherein R is selected from hydrogen, hydroxy, C$_1$-C$_4$-alkoxy, benzyloxy or substituted benzyloxy, NR$^y$R$^z$ wherein R$^y$ and R$^z$ are the same or different and selected from hydrogen, C$_1$-C$_4$-alkyl, methoxy, or R$^y$, R$^z$ are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, to form the compound of Formula $V^A$

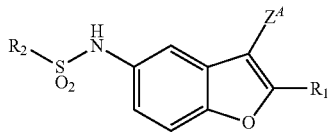

Formula $V^A$ wherein $R_1$, $R_2$ and $Z^A$ are the same as in Formula III and $IV^A$, d) if proviso $Z^A$ is COOH converting the compound of Formula $V^A$ to the compound of Formula II, by
i) converting the compound of Formula $V^A$ to give a compound of Formula VII

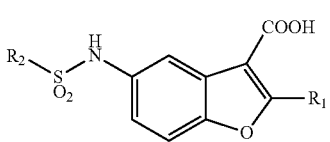

Formula VII wherein $R_1$ and $R_2$ are the same as in Formula $V^A$, by oxidation, hydrolysis or hydrogenolysis ii) optionally converting the compound of Formula VII to the compound of Formula VIII

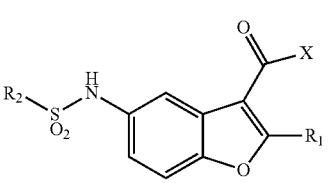

Formula VIII wherein $R_1$ and $R_2$ are as in Formula VII, and X is selected from halo or acyl, preferably chloro group, by treating with reactive sulfur, phosphorus, and acyl halogenides, preferably with thionyl chloride, oxalyl chloride, chloroformates or phosgene derivatives, iii) treating the compound of Formula $VI^B$

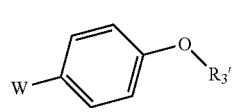

Formula $VI^B$ wherein W represents hydrogen, chloro, bromo or iodo and $R_3'$ is hydrogen, a phenol protecting group or $(CH_2)_n NR'R''$ wherein n is an integer 2-6 and R', R" are the same or different and selected from $C_1$-$C_6$-alkyl, benzyl, substituted benzyl or R', R" are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, with the compound of Formula VIII in the presence of strong acids or catalysts or promoters of substitution of W group, selected from acids or metal compounds, preferably from magnesium, boron, aluminium, gallium, indium, tin, iron compounds, optionally with additional catalysts selected from transition metals, preferably copper, palladium, ruthenium, optionally in the presence of ligands to give the compound of Formula $II^A$

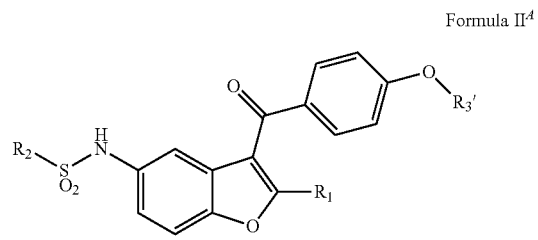

Formula $II^A$ iv) converting the compound of Formula $II^A$ to the compound of Formula II, proviso if $R_3$ is the same as $R_3'$ e) optionally converting the compound of Formula II into the pharmaceutically acceptable salt.

In a more special variation B1 of the embodiment B if the substituents W is bromo, the step is b iii) is executed by conversion of the compound of Formula $VI^B$ (W=Br) to an organometal intermediate, such organomagnesium, organoaluminium intermediate, or organoboron intermediate, which is further treated by the compound of Formula VIII in the presence of a transition metal catalyst, such as copper, palladium, ruthenium, optionally in the presence of ligands to give the compound of Formula $II^A$.

In another special variation B2 of the embodiment B if the substituents W is hydrogen, the compound of Formula $VI^B$ (W=H) is exposed in the step b iii) to Friedel-Crafts electrophilic substitution conditions using Friedel-Crafts catalysts, such as Lewis acids selected from aluminium trichloride, tin tetrachloride, or iron trichloride. It was surprisingly found that contrary to analogous transformations on nitro derivatives described in WO 05/066149 the substitution is highly regioselective yielding crude products of over 99 area % according to HPLC with orto by-product essentially bellow 1 area %.

In another special variation B3 of the embodiment B if the substituents W is hydrogen, the compound of Formula $VI^B$ (W=H) and the compound of Formula VII are coupled in the step b iii) in Friedel-Crafts electrophilic substitution conditions using strong Broensted acids selected from perchloric, sulfuric or phosphoric acid in acid anhydride media, preferable reaction mixture is concentrated phosphoric acid in trifluoroacetanhydride. Again the regioselectivity is very high, producing orto by-product far bellow 1 area %.

In a special but not limited case $R_1$ is selected from n-butyl, $R_2$ from methyl and $R_3$ from 3-(dibutylamino)-1-propyl.

According to a special embodiment C of the present invention the preparation of 3-aroyl-5-aminobenzofuran derivatives of Formula II:

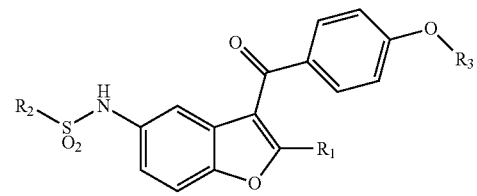

Formula II wherein $R_1$ is selected from $C_1$-$C_8$-alkyl, $R_2$ is selected from $C_1$-$C_8$-alkyl, fluorinated $C_1$-$C_8$-alkyl, phenyl, para substituted phenyl, and $R_3$ is hydrogen, a phenol protecting group or (CH$_2$)$_n$NR'R" wherein n is an integer 2-6 and R', R" are the same or different and selected from C$_1$-C$_6$-alkyl, benzyl, substituted benzyl or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, optionally in the form of pharmaceutically acceptable salts,
is performed by
a) treating the sulfonimidoquinone of Formula III

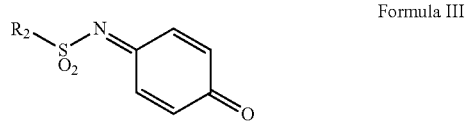

Formula III wherein R$_2$ is selected from C$_1$-C$_8$-alkyl, fluorinated C$_1$-C$_8$-alkyl, phenyl, para substituted phenyl,
with the compound of Formula IX:

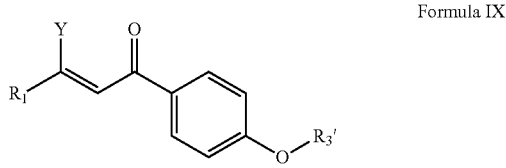

Formula IX wherein R$_1$ is selected from C$_1$-C$_8$-alkyl,
Y is selected from
hydroxy, C$_1$-C$_2$-alkoxy, phenoxy,
—OSi(R$^a$)$_3$ wherein R$^a$ is the same or different and selected from C$_1$-C$_4$-alkyl or phenyl,
—OSO$_2$R$^b$ wherein R$^b$ selected from unsubstituted or fluorinated C$_1$-C$_4$-alkyl, or phenyl, —OP(O)(OR$^b$)$_2$ wherein R$^c$ is selected from C$_1$-C$_4$-alkyl, or phenyl, or
di-C$_1$-C$_4$-alkylamino, pyrrolidino, piperidino, morpholino, and
R$_3$' is hydrogen, a phenol protecting group or (CH$_2$)$_n$NR'R" wherein n is an integer 2-6 and R', R" are the same or different and selected from C$_1$-C$_6$-alkyl, benzyl, substituted benzyl or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl,
in the presence of Broensted or Lewis acid, such as sulfuric acid, acetic acid, zinc cation, preferably in the presence of trityl cation to give the compound of Formula II$^A$

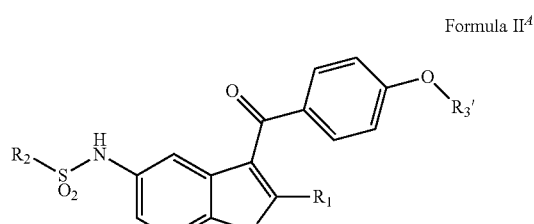

Formula II$^A$ b) converting the compound of Formula II$^A$ to the compound of Formula II, proviso if R$_3$ is the same as R$_3$'.

c) optionally converting the compound of Formula II into the pharmaceutically acceptable salt.

The condensation to benzofuran derivatives of Formula II$^A$ according to embodiment C occurs via unstable open form of Formula XIV irrespective to the activating-directing group Y.

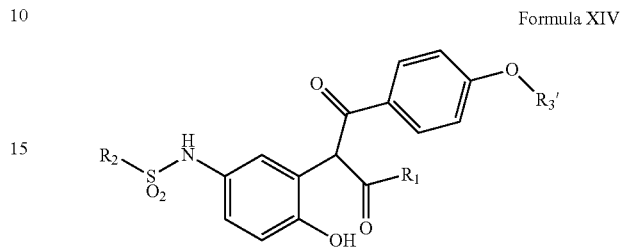

Formula XIV

The surprising removal of group Y and lability of in situ resulted intermediate of Formula XIV may complicate the condensation with considerable drop of yields. So it is more convenient to stabilize the intermediate state by using basic condition and to apply a two-step approach to accomplish the synthesis of the benzofuran system. In basic conditions the starting compound of Formula IX may be in its basic form (Y=OH), which is in its natural state predominantly in diketo form of Formula XII.

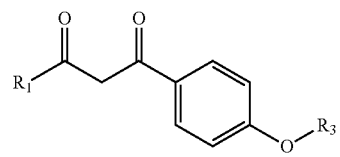

Thus, according to the preferable special option C1 of the embodiment C the preparation of 3-aroyl-5-aminobenzofuran derivatives of Formula II:

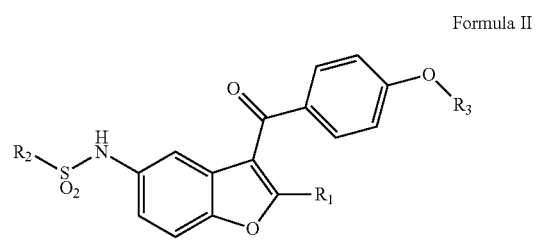

Formula II wherein R$_1$ is selected from C$_1$-C$_8$-alkyl, R$_2$ is selected from C$_1$-C$_8$-alkyl, fluorinated C$_1$-C$_8$-alkyl, phenyl, para substituted phenyl, and R$_3$ is hydrogen, a phenol protecting group or (CH$_2$)$_n$NR'R" wherein n is an integer 2-6 and R', R" are the same or different and selected from C$_1$-C$_6$-alkyl, benzyl, substituted benzyl or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, optionally in the form of pharmaceutically acceptable salts, is performed by a1) treating the sulfonimidoquinone of Formula III

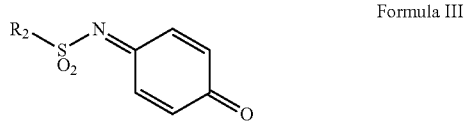

Formula III wherein R$_2$ is selected from C$_1$-C$_8$-alkyl, fluorinated C$_1$-C$_8$-alkyl, phenyl, para substituted phenyl, with the compound of Formula XII:

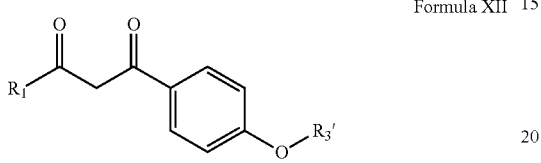

Formula XII wherein R$_1$ is selected from C$_1$-C$_8$-alkyl,
R$_3$' is hydrogen, a phenol protecting group or (CH$_2$)$_n$NR'R" wherein n is an integer 2-6 and R', R" are the same or different and selected from C$_1$-C$_6$-alkyl, benzyl, substituted benzyl or R', R" are fused to a link —(CH$_2$)$_m$—V—(CH$_2$)$_2$— wherein m is an integer from 1-3, and —V— is —CH$_2$—, —O— or —NR'''— wherein R''' is hydrogen, methyl or ethyl, in the presence of bases selected from tertiary amines, alkoxides, or hydrides, preferably from triethylamine or sodium methoxide a2) optionally treating the mixture by conventional methods, including at least one of the operations selected from neutralising the base, removing reagents and solvents, isolating the intermediate, purification, and redissolving, wherein conventional methods may include filtrations, extractions, evaporations, crystallisations and/or column chromatography a3) treating the obtained mixture with a base selected from tertiary amines and a Lewis acid, selected from titanium, tin, manganese, nickel, iron or zinc cation, most preferably with anhydrous zinc chloride, to give the compound of Formula II$^A$

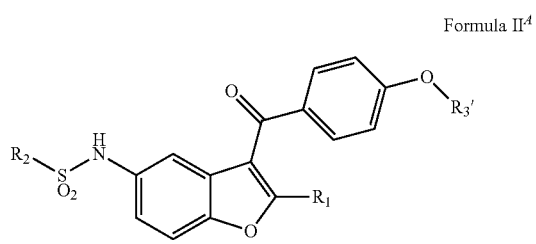

Formula II$^A$ b) converting the compound of Formula II$^A$ to the compound of Formula II, proviso if R$_3$ is the same as R$_3$'.

c) optionally converting the compound of Formula II into the pharmaceutically acceptable salt.

The intermediate of Formula XIV, resulted in the step a1) is unstable per se in the conditions of steps a1) and a2) and is submitted to retro-Claisen rearrangements to stable intermediates XV and XVI (Scheme 11).

Scheme 11

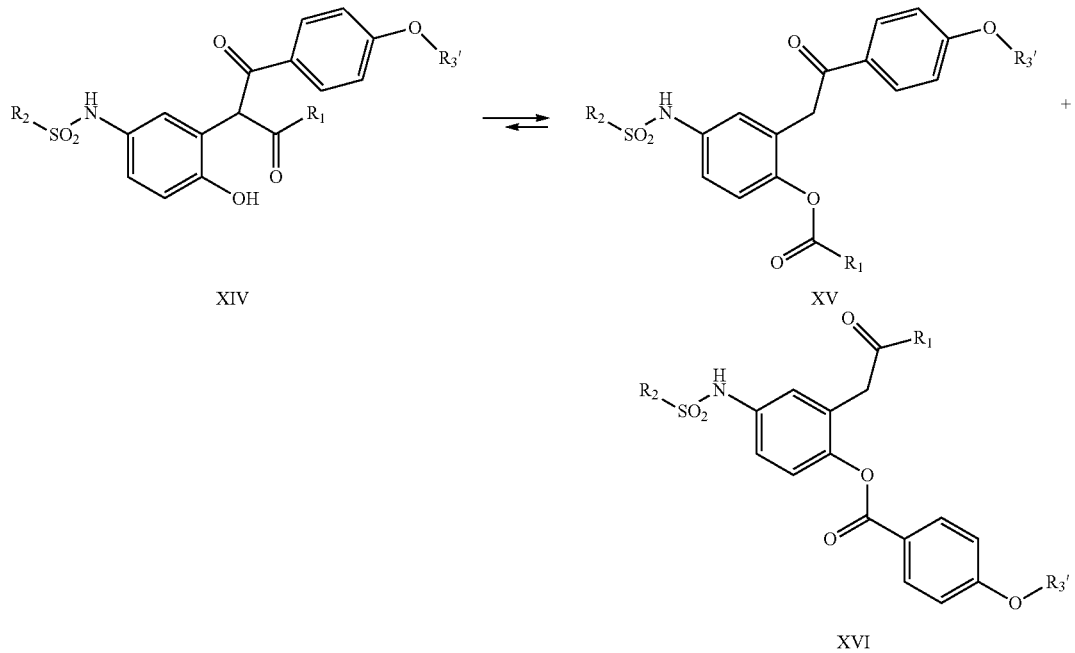

Surprisingly regardless to the ratio of intermediates XIV, XV and XVI their mixture is uniformly transformed to the compound of Formula II$^A$ in the presence of Lewis acid in conditions of the step a3) with high regioselectivity. A content of 2,3-regioisomer of Formula XVII preferably does not exceed 5%, more preferably 2%, most preferably 1% in the crude product of Formula II$^A$. The stability of retro-Claisen intermediates and their surprising regioselective conversion to 3-aroyl substituted benzofurans leads to better yields in the option C1 in comparison to the option C.

Formula XVII

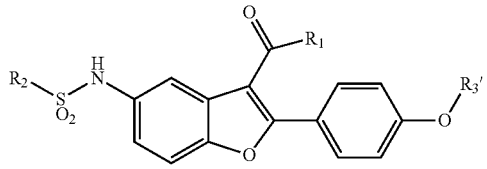

In a special but not limited case $R_1$ is selected from n-butyl, $R_2$ from methyl and $R_3$ from 3-(dibutylamino)-1-propyl.

The line "converting the compound of Formula V to the compound of Formula II, proviso if the Formula II represents the same structure as Formula V" in the step b) of the presented embodiment of the invention is described in more special options A, B, and C in steps of a) and b). These options are not intended to limit in any way the invention.

The line "converting the compound of Formula $II^A$ to the compound of Formula II, proviso if $R_3$ is the same as $R_3$'" in last paragraphs of step b) of special options A, B, and C is representative for examples wherein working substituents defined as $R_3$' are not the same as the final substituents defined as $R_3$. The working substituents as mentioned herein are substituents of starting compounds or intermediates entering the reactions of the invention. Such substituents are later removed and/or exchanged by a substituent, which characterises the final product. The working substituents are selected on the basis of inertness in the conditions of reactions of the invention, easier availability of starting compounds or better yields in particular steps.

Thus, the compound of Formula $II^A$,

Formula $II^A$

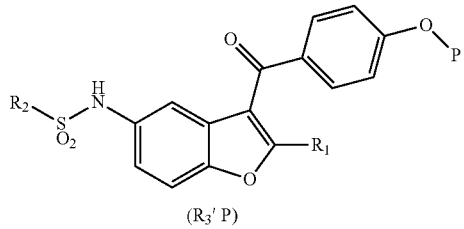

($R_3$' P)

wherein $R_1$ is selected from $C_1$-$C_8$-alkyl, $R_2$ is selected from $C_1$-$C_8$-alkyl, fluorinated $C_1$-$C_8$-alkyl, phenyl, para substituted phenyl, $R_3$' is a phenol protecting group P, selected from methyl, arylmethyl, $C_1$-$C_4$-alkoxymethyl, unsubstituted or substituted $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, or $OSi(R^a)_3$ wherein $R^a$ is the same or different and selected from $C_1$-$C_4$-alkyl or phenyl,
is transformed to the compound of Formula II Formula II

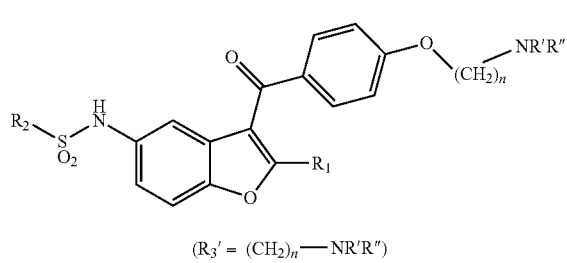

($R_3$' = $(CH_2)_n$—NR'R'')

wherein $R_3$ is selected from $(CH_2)_n$NR'R'' wherein n is an integer 2-6 and R', R'' are the same or different and selected from $C_1$-$C_6$-alkyl, benzyl, substituted benzyl or R', R'' are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, by f) deprotecting with corresponding reagents, preferably $OSi(R^a)_3$ is deprotected by treatment with fluoride anion, arylmethyl is removed by catalytic hydrogenolysis or $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl is removed by mild hydrolysis, to give phenol of Formula IIa ($R_3$'=H)

Formula $II^A$

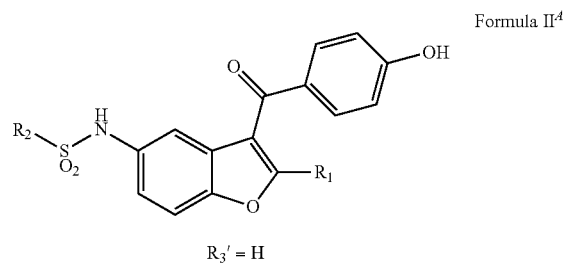

$R_3$' = H g) substituting the phenolic hydroxyl group by the compound of formula L-$(CH_2)_n$-A, wherein L is a leaving group, selected from halo or $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, preferably halo and A is another leaving group L' or NR'R'' wherein n is an integer 2-6 and R', R'' are the same or different and selected from $C_1$-$C_6$-alkyl, benzyl, substituted benzyl or R', R'' are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, wherein L and L' represent leaving groups in reactions of nucleophilic substitution and are the same or different, preferably different and should differ each from each in ability of being substituted, to give the compound Formula $II^A$

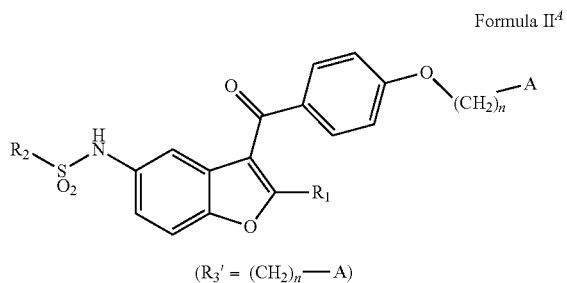

($R_3$' = $(CH_2)_n$—A)

h) optionally if A is the leaving group L' further treating with the amine HNR'R'' wherein n is an integer 2-6 and R', R'' are the same or different and selected from $C_1$-$C_6$-alkyl, benzyl, substituted benzyl or R', R'' are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl.

In options A, B, C wherein the working substituent $R_3$' is hydrogen, the step d) is omitted.

In options A, B, C wherein the working substituent $R_3$' is the final substituents $R_3$, steps d), e), and f) are omitted. In these particular options of the embodiment the starting compound of Formula VI

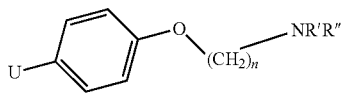

Formula VI wherein U is selected from hydrogen, chloro, bromo, iodo or acetyl, and R', R" are the same or different and selected from $C_1$-$C_6$-alkyl, benzyl, substituted benzyl or R', R" are fused to alkylene —$(CH_2)_m$— wherein m is integer 4-6, or R', R" are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, is prepared by g) treating of the compound of Formula XI

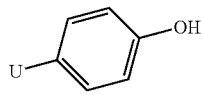

Formula XI by the compound of formula L-$(CH_2)_n$-A, wherein L is a leaving group, selected from halo or $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, preferably halo and A is another leaving group L' or NR'R" wherein n is an integer 2-6 and R', R" are the same or different and selected from $C_1$-$C_6$-alkyl, benzyl, substituted benzyl or R', R" are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, wherein L and L' represent leaving groups in reactions of nucleophilic substitution and are the same or different, preferably different and should differ in ability of being substituted, to give the compound

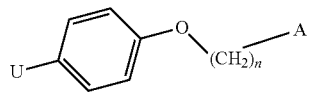

Formula IV$^E$ wherein U and A are the same as above, h) optionally if A is the leaving group L' by further treating with the amine HNR'R" wherein n is an integer 2-6 and R', R" are the same or different and selected from $C_1$-$C_6$-alkyl, benzyl, substituted benzyl or R', R" are fused to —$(CH_2)_2$—NR'''—$(CH_2)_2$—, wherein R''' is hydrogen, methyl or ethyl.

In a special option of the embodiment A the starting compound of Formula IV$^A$

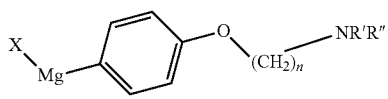

Formula IV$^A$ wherein X is halo, n is an integer 2-6 and R', R" are the same or different and selected from $C_1$-$C_6$-alkyl, benzyl, substituted benzyl or R', R" are fused to alkylene —$(CH_2)_m$— wherein m is integer 4-6, or R', R" are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, is prepared from the compound of Formula VI

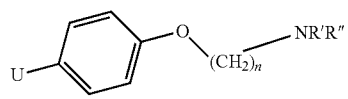

Formula VI wherein U is selected from halo, preferably bromo, by treating with elemental magnesium or by transmetalation with $R^M$MgX wherein R is $R^M$ is methyl, ethyl or vinyl and X is halo.

In another special option of the embodiment B the starting compound of Formula IV$^B$

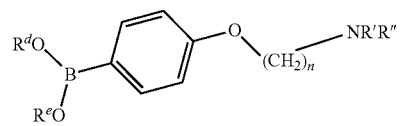

Formula IV$^B$ wherein n is an integer 2-6 and $R^d$ and $R^e$ are same or different and selected from hydrogen, $C_1$-$C_4$-alkyl or are fused linear or branched $C_2$-$C_6$-alkylene, and R', R" are the same or different and selected from $C_1$-$C_6$-alkyl, benzyl, substituted benzyl or R', R" are fused to alkylene —$(CH_2)_m$— wherein m is integer 4-6, or R', R" are fused to —$(CH_2)_2$—NR'''—$(CH_2)_2$—, wherein R''' is hydrogen, methyl or ethyl, is prepared from the compound of Formula VI

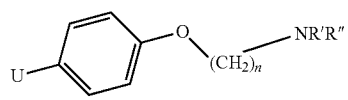

Formula VI wherein U is selected from halo, preferably bromo, by treating with boron reagent of formula BX'OR$^d$OR$^e$ wherein $R^d$ and $R^e$ are same or different and selected from hydrogen, $C_1$-$C_4$-alkyl or are fused linear or branched $C_2$-$C_6$-alkylene and X' is halo, acyloxy or $C_1$-$C_4$-alkoxy, preferably with trimethyl or triisopropyl borate.

In another special option of the embodiment B the starting compound of Formula IV$^C$

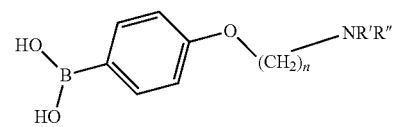

Formula IV$^C$ is prepared by hydrolysis of the compound of Formula IV$^B$.

In a special option of the embodiment C the starting compound of Formula IX$^C$

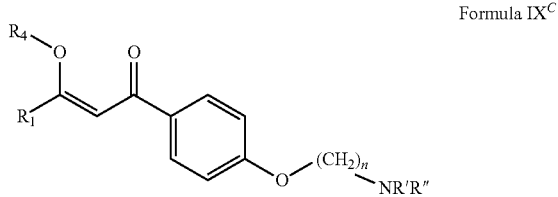

Formula IX$^C$ wherein $R_1$ is selected from $C_1$-$C_8$-alkyl, n is an integer from 2-6 and $R_4$ is selected from —Si($R^a$)$_3$ wherein $R^a$ is the same or different and selected from $C_1$-$C_4$-alkyl or phenyl, —SO$_2R^b$ wherein $R^b$ selected from unsubstituted or fluorinated $C_1$-$C_4$-alkyl, or phenyl, —P(O)(OR$^c$)$_2$ wherein $R^c$ is selected from $C_1$-$C_4$-alkyl, or phenyl, or R', R" are the same or different and selected from $C_1$-$C_6$-alkyl, benzyl, substituted benzyl, or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, is prepared by i) treating of the compound of Formula VI

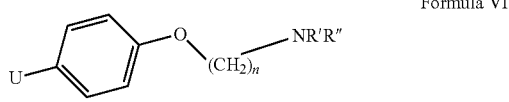

Formula VI wherein U is selected from acetyl and R', R" are the same or different and selected from $C_1$-$C_6$-alkyl, benzyl, substituted benzyl, or R', R" are fused to —(CH$_2$)$_2$—NR'"—(CH$_2$)$_2$—, wherein R'" is hydrogen, methyl or ethyl, with an ester of formula $R_1$—CO-A' wherein $R_1$ is selected from $C_1$-$C_8$-alkyl, and A' is $C_1$-$C_4$-alkoxy, $C_1$-$C_8$-acyloxy, halo or benzotriazolyloxy in presence of a base, selected from alkali or earth alkali metal, hydrides, amides, alkoxides or hydroxides to give a compound of Formula XII$^C$

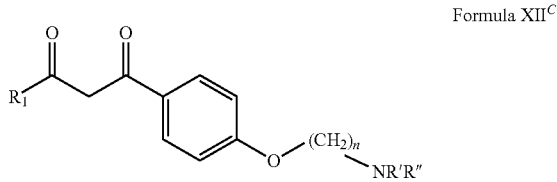

Formula XII$^C$ wherein $R_1$, R', R" and n are the same as above j) treated by a compound of formula $R_4$X wherein $R_4$ is the same as above and X is halo, in the presence of a base preferably in the presence tertiary amine.

In another special option of the embodiment C the starting compound of Formula X$^D$

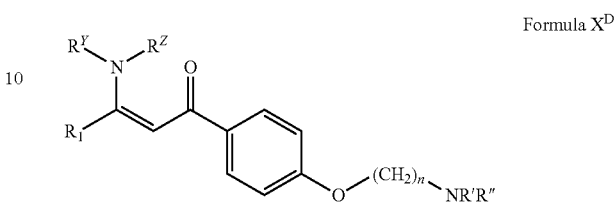

Formula X$^D$ wherein $R_1$ is selected from $C_1$-$C_8$-alkyl, n is an integer from 2-6 and $R^yR^z$ and R', R" are the same or different and selected from $C_1$-$C_6$-alkyl, benzyl, substituted benzyl or $R^y$, $R^z$ and R', R" respectively are fused to alkylene —(CH$_2$)$_m$— wherein m is integer 4-6, or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, is prepared by k) treating of the compound of Formula VI

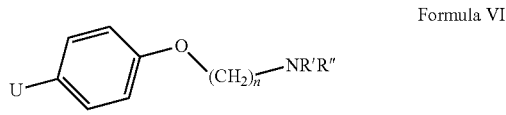

Formula VI wherein U is selected from acetyl and R', R" are the same or different and selected from $C_1$-$C_6$-alkyl, benzyl, substituted benzyl, or R', R" are fused to a link —(CH$_2$)$_m$—V—(CH$_2$)$_2$— wherein m is an integer from 1-3, and —V— is —CH$_2$—, —O— or —NR'"— wherein R'" is hydrogen, methyl or ethyl, with an amide of formula $R_1$—CO—NR$^y$R$^z$, preferably in an activated form of an acetal of Formula XIII

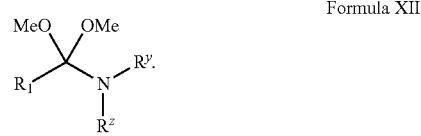

Formula XII or with an ortho ester $R_1$C(OR$^o$)$_3$ in the presence of amine HNR$^y$R$^z$, wherein R$^o$ is selected from methyl or ethyl and $R_1$, R$^y$ and R$^z$ are the same as in Formula X$_D$.

In a special but not limited case of the embodiment A the compound of Formula II ($R_1$ is n-butyl, $R_2$ is methyl, $R_3$ is (CH$_2$)$_n$NR'R"; n is 3, R' and R" is n-butyl) is prepared according to Scheme 6.

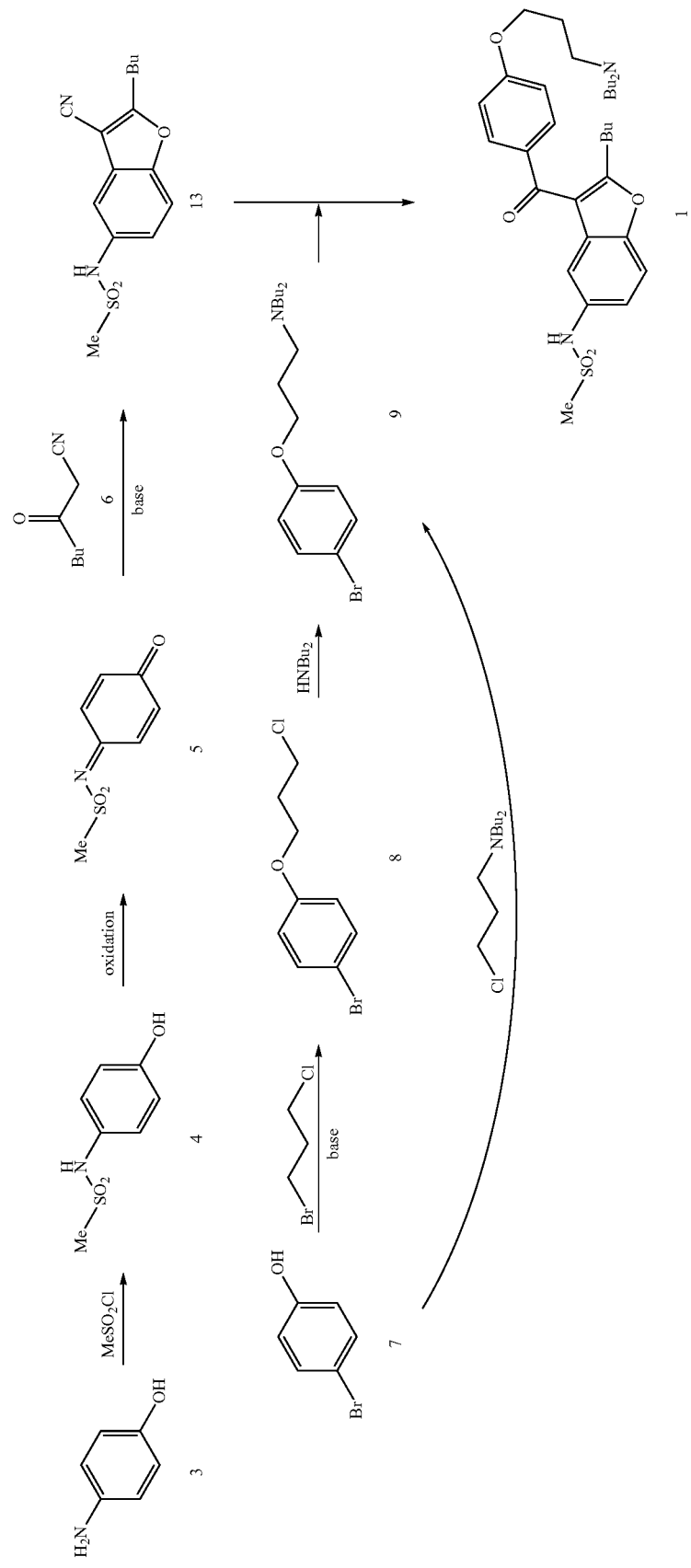

In a special but not limited case of the embodiment B the compound of Formula II ($R_1$ is n-butyl, $R_2$ is methyl, $R_3$ is $(CH_2)_n NR'R''$; n is 3, R' and R'' is n-butyl) is prepared according to Scheme 7.

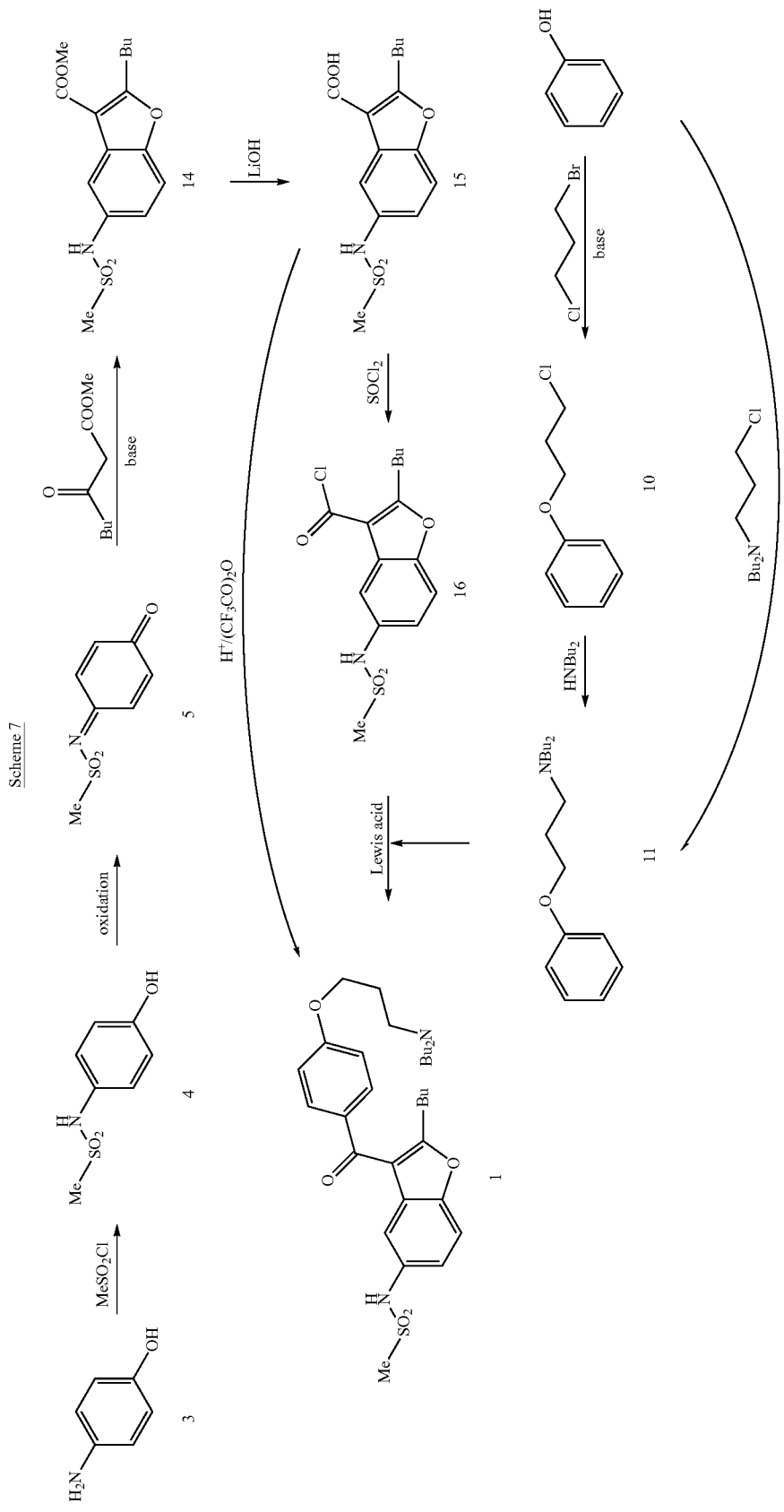

In another special branch of the embodiment B the compound of Formula II ($R_1$ is n-butyl, $R_2$ is methyl, $R_3$ is $(CH_2)_n NR'R''$; n is 3, R' and R'' is n-butyl) is prepared according to Scheme 8.

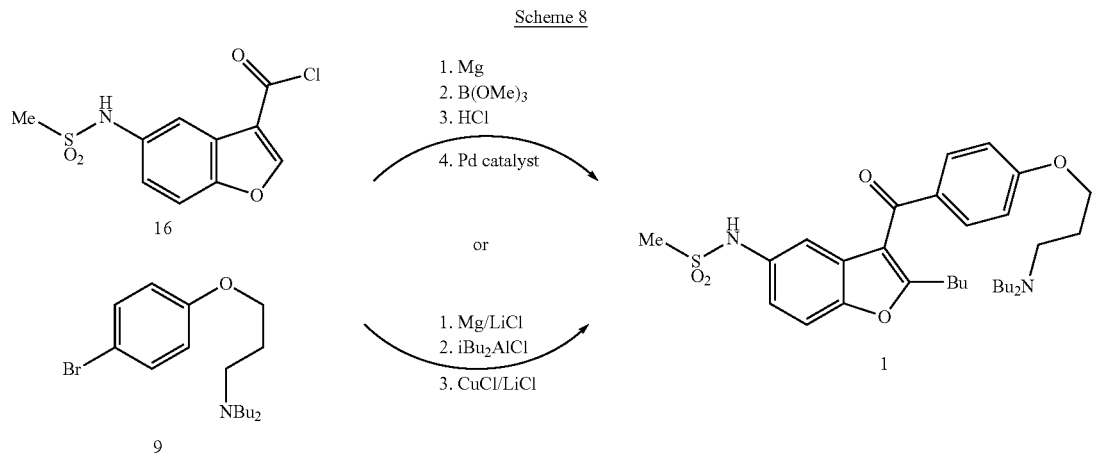

In a special but not limited case of the embodiment C the compound of Formula II ($R_1$ is n-butyl, $R_2$ is methyl, $R_3$ is $(CH_2)_n NR'R''$; n is 3, R' and R'' is n-butyl) is prepared according to Scheme 9.

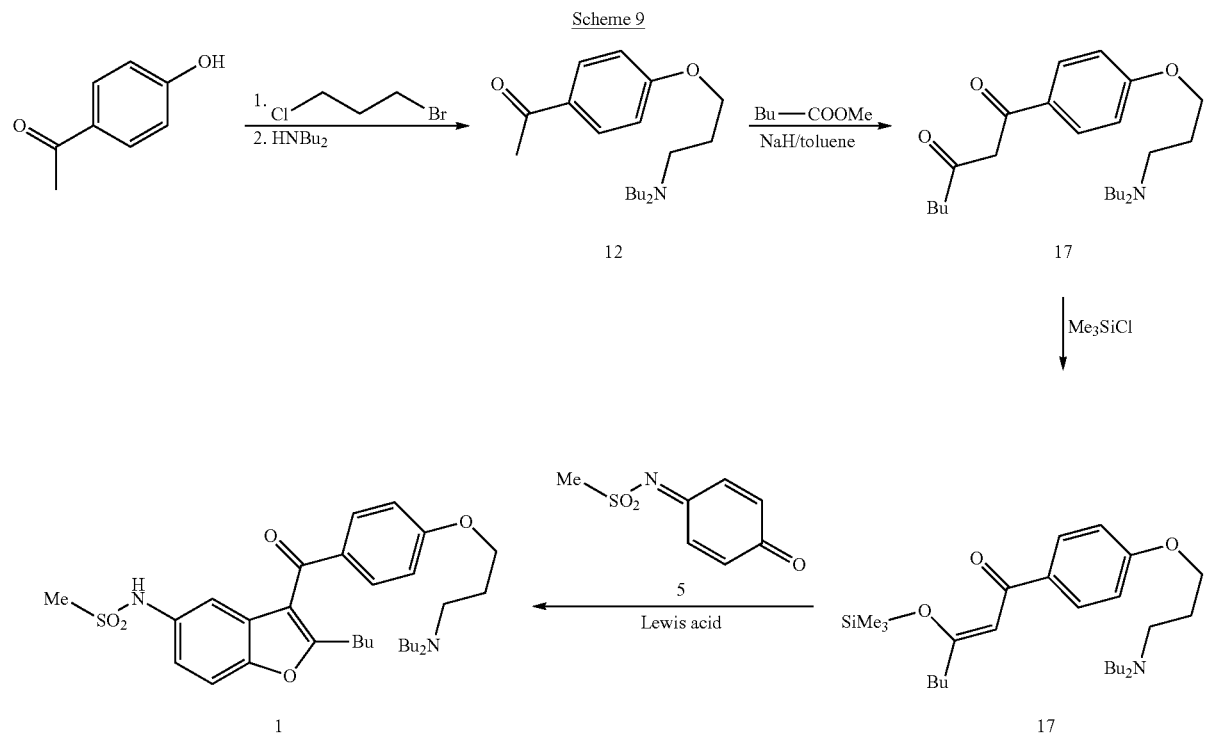

In another special limited of the embodiment C the compound of Formula II ($R_1$ is n-butyl, $R_2$ is methyl, $R_3$ is $(CH_2)_n NR'R''$; n is 3, R' and R'' is n-butyl) is prepared according to Scheme 10.

Scheme 10
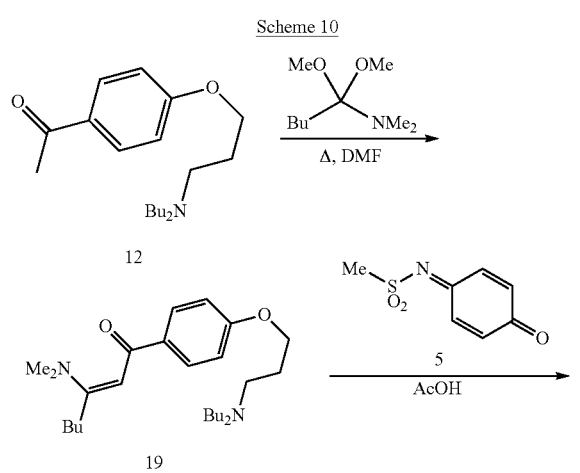
In another special limited of the embodiment C1 the compound of Formula II ($R_1$ is n-butyl, $R_2$ is methyl, $R_3$ is $(CH_2)_nNR'R''$; n is 3, R' and R'' is n-butyl) is prepared according to Scheme 11.
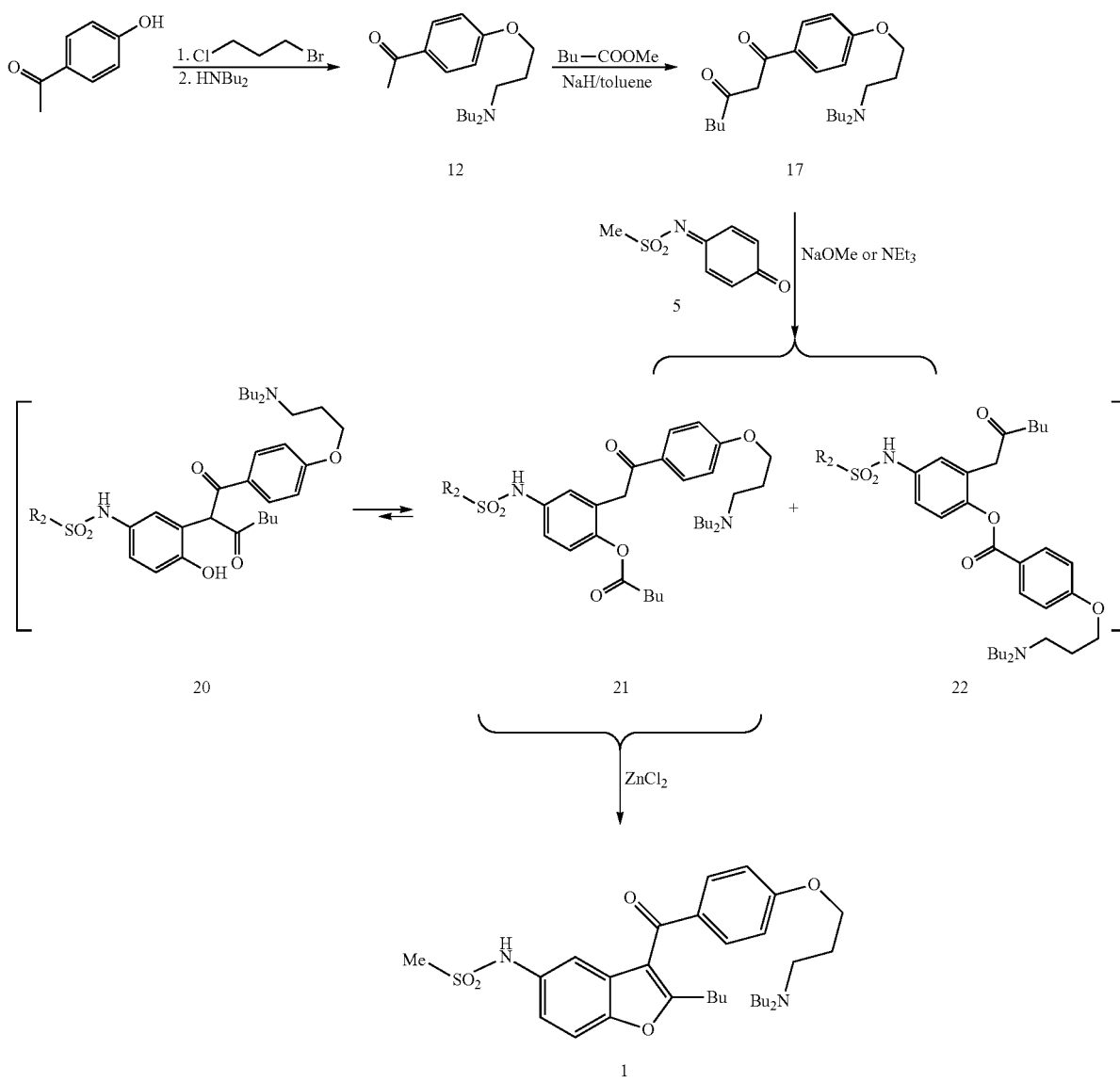

In all subroutes of the invention, presented in Schemes 6-11 commercially available p-aminophenol is used as starting material, so there is no need to use potential genotoxic nitro intermediates in any step. Furthermore, the methanesulfonamide group is resistant to all reaction steps used in the synthesis of the invention, so there is no need for special protection of amino group, which has to be later removed and replaced by a sulfonyl group. Therefore, the invention represents the shortest non-nitro constituting synthesis of 3-aroyl-5-aminobenzofuran containing anti arrhythmic drugs and is comparative in this view to nitro substituted intermediates containing procedures or even shorter. The approach also guarantees a final pharmaceutical product free from nitro containing genotoxic impurities and free from even more genotoxic by-products such as nitroso compounds.

The Friedel-Crafts reaction, which is the routine approach in the synthesis of 3-aroylbenzofurans may be applied as an option in the synthesis of the present invention, however, there is sufficient room for the possibility to apply reactions conditions more compatible with industrial standard equipment.

For preparing a pharmaceutical composition comprising the compounds (1) or (2) or derivatives thereof disclosed herein, or respective pharmaceutically acceptable salts thereof as active ingredients, first the respective pharmaceutical composition or pharmaceutically acceptable salts thereof is provided by the process as described above.

Then, the thus prepared respective pharmaceutical composition or pharmaceutically acceptable salts thereof is suitably admixed with at least one suitable pharmaceutically acceptable excipient. Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology.

Preferably, excipients may be selected from the group consisting of lactose, microcrystalline cellulose, cellulose derivatives, e.g. hydroxypropylcellulose, polyacrylates, calcium carbonate, starch, colloidal silicone dioxide, sodium starch glycolate, talc, magnesium stearate, polyvinylpyrrolidone, polyethylene glycol and other excipients known in the field of the pharmaceutical technology.

EXPERIMENTAL PROCEDURES

Following examples further illustrate the invention. They are provided for illustrative purposes only and are not intended to limit in any way the invention.

Example 1

Synthesis of N-(4-oxocyclohexa-2,5-dienylidene) methanesulfonamide (5)

To a stirred suspension of 19 g of 4-(methylsulfonylamino)phenol (4, 1 eq., prepared according to *J. Med. Chem.* 1999, 42, 1041-1052) in 70 ml of glacial acetic acid is added at room temperature 44 g of lead tetraacetate (1.02 eq) in several portions over 15 minutes. The resulting mixture is stirred for 25 minutes. 0.5 ml of ethylene glycol is added and the mixture is stirred for 15 minutes. Then 5 ml of ethylene glycol is added and the stirring is continued for 45 minutes. The mixture is cooled down to 8° C., the product is filtered off, washed with cold acetic acid and dried to give 14 g of product (75% yield).

Example 2

Synthesis of N-(3-(4-bromophenoxy)propyl)-N-butylbutan-1-amine (9)

Procedure A

To a stirred solution of commercial available 4-bromophenol (7, 1 eq.) in N,N-dimethylformamide is added potassium carbonate (1.25 eq.) The mixture is heated to 100° C. and then the 1-dibutylamino-3-chloropropane (prepared according to Swiss Pat. CH221596 or *Helv. Chim. Acta* 1941, 24, 209.) is added over 20 minutes. After stirring for 1 h at 100° C. the mixture is cooled to 25° C. and the inorganic salts are filtered off. The filtrate is concentrated under reduced pressure to obtain the title compound in 90% yield.

Procedure B

A mixture of commercially available 4-bromophenol (7, 6.92 g, 1 eq), potassium carbonate (5.53 g, 1 eq.) and 1-bromo-3-chloropropane (6.77 g, 1.07 eq) in 2-butanone (50 ml) is heated at reflux overnight. The inorganic salts are filtered off. The filtrate is evaporated under reduced pressure. The residue is partitioned between dichloromethane and 1% aqueous NaOH solution. The organic phase is dried ($Na_2SO_4$) and evaporated under reduced pressure. Diisopropyl ether is added and the solution is stirred for 1 hour at 0° C. Small amount of solids is filtered off and the filtrate is evaporated under reduced pressure to give 9.4 g of 1-bromo-4-(3-chloropropoxy)benzene (8, 94% yield).

1-Bromo-4-(3-chloropropoxy)benzene (8, 4 g, 1 eq.) is dissolved in 2-butanone and potassium iodide (1.33 g, 0.5 eq.), potassium carbonate (4.42 g, 2 eq.) and N,N-dibutylamine (3.1 g, 1.5 eq.) is added. The mixture is heated at reflux for 3 days. The reaction mixture is evaporated under reduced pressure. Water is added and the product is extracted with ethyl acetate. Organic phase is dried ($Na_2SO_4$) and evaporated under reduced pressure. The product is purified by column chromatography on silica gel with ethyl acetate/heptane (1:2 v/v) mixture to give 4.1 g (75% yield from 8).

Example 3

Synthesis of N-(3-phenoxypropyl)-N-butylbutan-1-amine (11)

Potassium carbonate (14.7 g, 2 eq.) is suspended in acetone. Phenol (5 g, 1 eq.) and 1-bromo-3-chloropropane (10 g, 1.2 eq.) are added and the mixture is heated at reflux over night. The solvents were evaporated under reduced pressure. 1 M aqueous NaOH solution is added and the product is extracted with ethyl acetate. Organic phase is washed with water, dried ($Na_2SO_4$) and evaporated under reduced pressure to give 9.8 g of (3-chloropropoxy)benzene (10, 98% yield).

(3-Chloropropoxy)benzene (10, 2.74 g, 1 eq.) is dissolved in 2-butanone and potassium iodide (1.33 g, 0.5 eq.), potassium carbonate (4.42 g, 2 eq.) and N,N-dibutylamine (3.1 g, 1.5 eq.) is added. The mixture is heated at reflux for 3 days. The reaction mixture is evaporated under reduced pressure. Water is added and the product is extracted with ethyl acetate. Organic phase is dried ($Na_2SO_4$) and evaporated under reduced pressure. The product is purified by column chromatography on silica gel with ethyl acetate/heptane (1:2 v/v) mixture to give 2.3 g (55% yield from 10).

Example 4

Synthesis of 1-(4-(3-(dibutylamino)propoxy)phenyl) ethanone (12)

20.4 g of 1-(4-hydroxyphenyl)ethanone (1.0 eq), 60 ml (4 eq) of 3-bromo-1-chloropropane, and 124.2 g (6 eq) of $K_2CO_3$, are added to 200 ml acetone and the mixture is refluxed for 20 hrs. Acetone is partially removed and the residue is diluted by water and dichloromethane. Organic phases are combined and the solvent and the excess of 3-bromo-1-chloropropane are distilled off to give 28.7 g (90%) of crude 4-(3-chloropropoxy)acetophenone, which may be purified by distillation or column chromatography.

5 g (1 eq) of the crude product of the previous step and 15 ml (3.8 eq) of dibutylamine, are reflux for 5 h, the mixture is diluted by dichloromethane and washed twice with water. Solvent is removed to give 7.5 g of the product, which contains some amounts of dibutylamine, which can be removed by distilling off.

Example 5

Synthesis of N-(2-butyl-3-cyanobenzofuran-5-yl) methanesulfonamide (13)

To a solution of N-(4-oxocyclohexa-2,5-dienylidene) methanesulfonamide (5, 1 eq.) and 3-oxoheptanenitrile (6, 1.1 eq.) (prepared according to Org. Prep. Proced. Intl., 1985, 17, 235) in dioxane is added sodium methoxide (0.1 eq.) and the mixture is allowed to stand at room temperature for 30 minutes. Then reaction mixture is poured into water and precipitation occurs. The solid adduct is dispersed in 70% aqueous sulfuric acid and stirred at room temperature as long as the adduct is consumed. Then the reaction mixture is poured on ice, ethyl acetate is added, and the layers are separated. Evaporation of the solvent followed by chromatography on silica gel provides the pure product in 6% yield.

Example 6

Synthesis of methyl 2-butyl-5-(methylsulfonamido) benzofuran-3-carboxylate (14)

To a solution of N-(4-oxocyclohexa-2,5-dienylidene) methanesulfonamide (5, 1 eq.) and commercially available methyl 3-oxoheptanoate (1.1 eq.) in dioxane is added sodium methoxide (0.1 eq.) and the mixture is allowed to stand at room temperature for 1 h. The reaction mixture is filtered and the filtrate is concentrated in vacuo to a small volume. The crude residue is heated in hydrochloric acid under reflux for several hours. After the reaction is complete the mixture is cooled, the product is removed by filtration to get a product in 80% yield, which is optionally purified by recrystallisation.

Example 7

Synthesis of 2-butyl-5-(methylsulfonamido)benzofuran-3-carboxylic acid (15)

To a solution of N-(4-oxocyclohexa-2,5-dienylidene) methanesulfonamide (5, 1 eq.) and commercially available 3-oxoheptanoic acid (1.1 eq.) in dioxane is added sodium methoxide (0.1 eq.) and the mixture is allowed to stand at room temperature for 1 h. The reaction mixture is filtered and the filtrate is concentrated in vacuo to a small volume. The crude product is solidified by cooling the solution and adding a small amount of heptane. A suspension of the obtained solid is heated in hydrochloric acid under reflux for several hours. After the reaction is complete the mixture is cooled, the product is removed by filtration and recrystallized in acetone to get a solid product in 70% yield.

Example 8

Synthesis of lithium salt of 2-butyl-5-(methylsulfonamido)benzofuran-3-carboxylic acid (15)

To a stirred solution of 1M LiOH (aq.) (1.0 eq.) in water and dioxan is slowly added methyl 2-butyl-5-(methylsulfonamido)benzofuran-3-carboxylate (14, 1.0 eq.) at room temperature. After stirring for 16 h, the sample is concentrated in vacuo, the residue is dissolved in water-acetonitrile (1:1) and the mixture is lyophilized to give the lithium salt as an off-white solid product in 95% yield.

Example 9

Synthesis of 2-butyl-5-(methylsulfonamido)benzofuran-3-carbonyl chloride (16)

To an access of thionyl chloride at 0° C. is added the 2-butyl-5-(methylsulfonamido)benzofuran-3-carboxylic acid (15) lithium salt (1.0 eq.) under a nitrogen atmosphere and the reaction is refluxed for several hours. The excess thionyl chloride is removed in vacuo and the crude product is triturated with toluene and evaporated. After dissolving the solid in tetrahydrofuran, charcoal is added, and the mixture is filtered through Celite. Concentration in vacuo provides a solid, which is then slurried with cold diethyl ether and collected by filtration. Drying in vacuo provides the title compound in 90% yield.

Example 10

Synthesis of N-(2-butyl-3-(4-(3-(dibutylamino) propoxy)benzoyl)benzofuran-5-yl) methanesulfonamide (1)

To a solution of N-(3-(4-bromophenoxy)propyl)-N-butylbutan-1-amine (1 eq.) in THF is added magnesium (1.5 eq.). The suspension is stirred and refluxed for about 1 h. After cooling the mixture to −78° C., trimethyl borate (1.2 eq.) is added. The reaction mixture is stirred at −78° C. for 2 h and then warmed to room temperature. The resulting mixture is quenched with 1N HCl and then washed with ethyl ether. Triethylamine is added to the aqueous layer and the resulting mixture is extracted several times with diethyl ether. The combined organic layers are dried over $Na_2SO_4$ and evaporated under reduced pressure to get crude 4-(3-(dibutylamino)propoxy) phenylboronic acid.

To a stirred mixture of $Na_2CO_3$ (1.6 eq.) and $PdCl_2$ (1.7 mol %) in acetone/water (1:1) is added sodium dodecyl sulfate (0.5 eq.) and the mixture is heated to 60° C. with stirring. To this mixture 4-(3-(dibutylamino)propoxy) phenylboronic acid (1.2 eq.) from the previous step and 2-butyl-5-(methylsulfonamido)benzofuran-3-carbonyl chloride (1.0 eq.) are added and the mixture is held at 60° C. for several hours. When the reaction is complete, the mixture is cooled to room temperature and the resulting suspension is extracted several times with diethyl ether. The combined organic layers are dried over $Na_2SO_4$ and evaporated under reduced pressure. Further purification of the product is achieved by flash column chromatography on silica gel to get a solid product in over 40% yield of both steps.

Example 11

Synthesis of N-(2-butyl-3-(4-(3-(dibutylamino) propoxy)benzoyl)benzofuran-5-yl) methanesulfonamide (1)

To a stirred mixture of anhydrous LiCl (1.5 eq.), and magnesium turnings (3.0 eq.) in freshly distilled THF under argon, is added a DIBAL-H solution (0.1 M solution in THF, 0.01 eq.). After heating for about 1 min and then cooling to 25° C., an i-Bu$_2$AlCl solution (1.4 eq. 0.8 M in heptane) is added. Finally, N-(3-(4-bromophenoxy)propyl)-N-butylbutan-1-amine (9, 1.25 eq.) is added in one portion at 25° C. After completion of the reaction at this temperature, the reaction mixture is transferred into a new flask and is cooled to −10° C. To the stirred mixture is added CuCN.2LiCl (1 M in THF, 0.10 eq.), and the reaction mixture is stirred for 5 min. After the addition of 2-butyl-5-(methylsulfonamido) benzofuran-3-carbonyl chloride (16, 1.0 eq.) the cooling bath is removed and the mixture is stirred for several hours at 25° C. The reaction is quenched with acetic acid at −30° C. and then kept at 25° C. for several minutes. The mixture is extracted several times with ethyl acetate, washed with aqueous saturated NaHCO$_3$, water, and saturated NaCl solution. The combined organic layers are dried over Na$_2$SO$_4$ and the solvents are removed under reduced pressure to furnish the crude product, which is further purified by column chromatography (SiO$_2$) to obtain the title compound.

Example 12

Synthesis of 1-(4-(3-(dibutylamino)propoxy)phenyl) heptane-1,3-dione (17)

Procedure A:
To a stirred solution of 1-(4-(3-(dibutylamino)propoxy) phenyl)ethanone (12, 1 eq.) in dry DMF under argon is added 60% NaH (1.5 eq.) in several portions to maintain the temperature between −5 to 0° C. After stirring at this temperature for 1 h, methyl pentanoate is added slowly and the reaction mixture is allowed to stir at ambient temperature for 4-5 h. When the reaction is complete, the mixture is poured into ice water, acidified with 2N HCl and extracted several times with ethyl acetate. The combined organic layers are washed with water, dried over anhydrous Na$_2$SO$_4$, filtered and concentrated in vacuo to give the crude product. Purification of this material by column chromatography (SiO$_2$) affords the title compound.
Procedure B
NaH (60% suspension in mineral oil, 3.5 eq) is suspended in toluene. Methyl valerate (2 eq) is added at ambient temperature. The solution is heated up to 100° C. and then the solution of 1-(4-(3-(dibutylamino)propoxy)phenyl)ethanone (12, 1 eq.) in toluene is added dropwise within 40 min. After complete addition the reaction mixture is refluxed for 2 h and then cooled down to 0° C. Methanol is added dropwise carefully to quench the excess of NaH followed by 10% H$_2$SO$_4$ solution and water. The layers are separated and the organic phase is washed with water, brine then dried and evaporated to give crude product as brown oil, which is further purified by column chromatography (SiO$_2$) to obtain the title compound in 81% yield.

Example 13

Synthesis of N-(2-butyl-3-(4-(3-(dibutylamino) propoxy)benzoyl)benzofuran-5-yl) methanesulfonamide (1)

To a stirred solution of 1-(4-(3-(dibutylamino)propoxy) phenyl)heptane-1,3-dione (17, 1.0 eq.) in toluene is added triethylamine (1.6 eq.). After stirring the solution for 2 h, trimethylchlorosilane (1.8 eq.) is added and the solution is stirred for several hours. When the reaction is complete, the solvent is removed in vacuo and heptane is added to the residue to give a suspension. The mixture is filtered under argon atmosphere. The filtrate is concentrated in vacuo to give (E/Z)-1-(4-(3-(dibutylamino)propoxy)phenyl)-3-(trimethylsilyloxy)hept-2-en-1-one (18), which is further used without purification.
The compound of previous step (18, 1.1 eq.) is diluted by dichloromethane, followed by addition of N-(4-oxocyclohexa-2,5-dienylidene)methanesulfonamide (5, 1 eq.) and trityl perchlorate (5-10 mol %). The mixture is then heated to 45° C. under nitrogen for several hours. When the reaction is complete, the mixture is partitioned between dichloromethane and water, and the aqueous layer is extracted several times with dichloromethane. The organic layers are combined, dried over anhydrous Na$_2$SO$_4$, filtered and concentrated in vacuo to give the crude product. Purification of this material by column chromatography (SiO$_2$) affords the title compound as a solid.

Example 14

Condensation of Azaquinone 5 with Diketone 17

To a solution of N-(4-oxocyclohexa-2,5-dienylidene) methanesulfonamide (5, 1 eq.) and 1-(4-(3-(dibutylamino) propoxy)phenyl)heptane-1,3-dione (17, 1.1 eq.) in dioxane is added sodium methoxide (0.1 eq.) and the mixture is allowed to stand at room temperature for 1 h. The reaction mixture is filtered and the filtrate is concentrated under vacuo to a small volume. The crude product is solidified by cooling the solution and adding a small amount of heptane. A suspension of the obtained solid is heated in hydrochloric acid under reflux for several hours. After neutralizing by sodium hydroxide solution, the product was extracted by dichloromethane, concentrated and purified by column chromatography (SiO$_2$) to give a mixture of retro-Claisen products 21 and 22 with minor amounts of N-(2-butyl-3-(4-(3-(dibutylamino)propoxy)benzoyl)benzofuran-5-yl) methanesulfonamide (1).

Example 15

Synthesis of N-(2-butyl-3-(4-(3-(dibutylamino) propoxy)benzoyl)benzofuran-5-yl) methanesulfonamide (1)

A stirred solution of 1-(4-(3-(dibutylamino)propoxy)phenyl)ethanone (16, 1 eq.) and 1,1-di-methoxy-N,N-dimethylpentan-1-amine (1 eq., prepared according to Ger. Pat. DE 2644556) in DMF is heated to 105° C. under nitrogen. After stirring for several hours at 105° C., solvent is removed under reduced pressure to give (E)-1-(4-(3-(dibutylamino)

propoxy)phenyl)-3-(di-methylamino)hept-2-en-1-one (19) as a residue, which is optionally purified by column chromatography.

The compound 19 of previous step (1 eq.) in DMF is added a solution of N-(4-oxocyclohexa-2,5-dienylidene) methanesulfonamide (5, 1 eq.) in DMF and acetic acid is added at room temperature under nitrogen. When the reaction is complete, the mixture is partitioned between diethyl ether and water, and the aqueous layer is extracted several times with diethyl ether. The organic layers are combined, dried over anhydrous Na$_2$SO$_4$, filtered and concentrated in vacuo to give the crude product. Purification of this material by column chromatography (SiO$_2$) affords the title compound as a greasy solid.

Example 16

Synthesis of N-(2-butyl-3-(4-(3-(dibutylamino) propoxy)benzoyl)benzofuran-5-yl) methanesulfonamide (1)

1-(4-(3-(Dibutylamino)propoxy)phenyl)heptane-1,3-dione (17, 1 eq) and N-(4-oxocyclohexa-2,5-dienylidene) methanesulfonamide (5, 1 eq) are dissolved separately in anhydrous dioxane. The solutions are placed in two separate syringes and are added dropwise to the solution of triethylamine (1 eq) in dioxane. After the addition the reaction mixture is stirred at room temperature. After the reaction is complete, the solvent is evaporated under reduced pressure. The residue is purified by column chromatography (SiO$_2$) to give a mixture of retro-Claisen products 21 and 22.

The purified material is dissolved in 1,2-dichloroethane and triethylamine (1.5 eq) and ZnCl$_2$ (1.1 eq) are added. The mixture is refluxed. After the reaction is complete the reaction mixture is allowed to cool down to room temperature and is then filtered through pad of Celite. The filtrate is concentrated to provide yellow foam, which is diluted in hexane and stirred. The solid was filtered and dried to give the title compound as a hydrochloride salt in 50% yield.

Example 17

Synthesis of N-(2-butyl-3-(4-(3-(dibutylamino) propoxy)benzoyl)benzofuran-5-yl) methanesulfonamide (1)

2-Butyl-5-(methylsulfonamido)benzofuran-3-carbonyl chloride (16, 1 eq) is dissolved in dichloromethane. N-(3-phenoxypropyl)-N-butylbutan-1-amine (11, 1 eq) and aluminum chloride (4.5 eq) are added. The mixture is refluxed overnight. The reaction mixture is then cooled to 25° C. and saturated aqueous solution of sodium bicarbonate is added slowly while stirring vigorously. Dichloromethane and potassium sodium tartrate solution are added and the phases are separated. The organic phase is washed with 1 M sodium hydroxide and water, dried over anhydrous Na$_2$SO$_4$ and evaporated to give the title compound in 72% yield.

Example 18

Synthesis of N-(2-butyl-3-(4-(3-(dibutylamino) propoxy)benzoyl)benzofuran-5-yl) methanesulfonamide (1)

Trifluoroacetic anhydride (60 eq) and 85% phosphoric acid (7 eq) are added to 2-butyl-5-(methylsulfonamido) benzofuran-3-carboxylic acid (15, 1 eq) followed by the addition of N-(3-phenoxypropyl)-N-butylbutan-1-amine (11, 1.2 eq). The mixture is refluxed for 20 hours and then the solvents are evaporated. The residue is dissolved in dichloromethane and added into a cold mixture of sodium hydroxide and dichloromethane. The pH is set to 8 and the phases are separated. The organic layer is washed with water dried over anhydrous Na$_2$SO$_4$ and evaporated to give the title compound in 70% yield.

The invention claimed is:

1. A process for the preparation of a compound of Formula V or a salt thereof

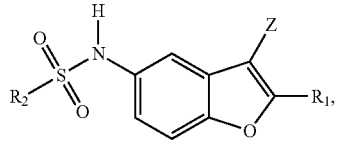

Formula V wherein

R$_1$ is selected from C$_1$-C$_8$-alkyl,

R$_2$ is selected from the group consisting of: C$_1$-C$_8$-alkyl, fluorinated C$_1$-C$_8$-alkyl, phenyl, and para substituted phenyl, and Z is cyano or C(O)R, wherein R represents a benzene ring having a halo substituent in none, one or both of the meta positions and having a fluoro, chloro, bromo, iodo, nitro, C$_1$-C$_8$-alkyl, substituted C$_1$-C$_8$-alkyl, hydroxy, C$_1$-C$_8$-alkoxy, substituted C$_1$-C$_8$-alkoxy, C$_1$-C$_8$-alkylamino, or substituted C$_1$-C$_8$-alkylamino substituent in para position, the process comprising a) treating a sulfonimidoquinone of Formula III

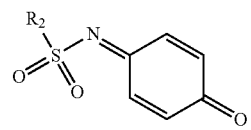

Formula III with a compound of Formula IV in enolic or ketonic tautomeric form,

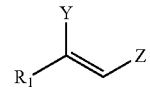

Formula IV wherein Y is selected from the group consisting of:

hydroxy, C$_1$-C$_2$-alkoxy, phenoxy,

—OSi(R$^a$)$_3$ wherein R$^a$ is the same or different and selected from the group consisting of: C$_1$-C$_4$-alkyl and phenyl, —OSO$_2$R$^b$ wherein R$^b$ is unsubstituted or fluorinated C$_1$-C$_4$-alkyl, or phenyl, and —OP(O)(OR$^c$)$_2$ wherein R$^c$ is selected from the group consisting of: C$_1$-C$_4$-alkyl, and phenyl, and Z is as defined above.

2. The process according to claim 1 wherein the compound of Formula V is a compound of Formula I

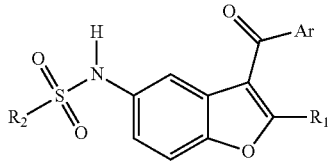

Formula I or a pharmaceutical acceptable salt thereof, wherein the compound of Formula III is treated with the compound of Formula IV wherein Z is C(O)Ar and Ar is a benzene ring having a halo substituent in none, one or both of the meta positions and having a fluoro, chloro, bromo, iodo, nitro, $C_1$-$C_8$-alkyl, substituted $C_1$-$C_8$-alkyl, hydroxy, $C_1$-$C_8$-alkoxy, substituted $C_1$-$C_8$-alkoxy, $C_1$-$C_8$-alkylamino or substituted $C_1$-$C_8$-alkylamino substituent in the para position.

3. The process according to claim 1 wherein the compound of Formula V is a compound of Formula II

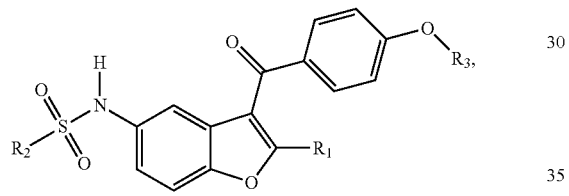

Formula II wherein $R_3$ is hydrogen; a phenol protected group selected from the group consisting of: methyl, arylmethyl, $C_1$-$C_4$-alkoxymethyl, unsubstituted or substituted $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, and OSi($R^a$)$_3$ wherein $R^a$ is the same or different and selected from the group consisting of: $C_1$-$C_4$-alkyl and phenyl; or (CH$_2$)$_n$NR'R", wherein n is an integer 2-6, and R' and R" are the same or different and selected from the group consisting of: $C_1$-$C_6$-alkyl, benzyl, and substituted benzyl, or R' and R" are fused by —(CH$_2$)$_m$—V—(CH$_2$)$_2$— wherein m is an integer from 1-3, and —V— is —CH$_2$—, —O— or —NR'''— wherein R''' is hydrogen, methyl or ethyl, the process comprising a) treating the sulfonimidoquinone of Formula III

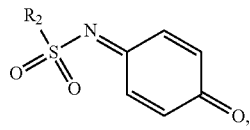

Formula III wherein $R_2$ is as defined above,
with a compound of Formula IX in enolic or ketonic tautomeric form,

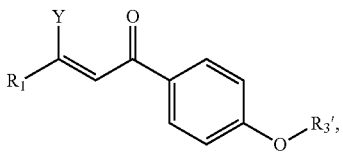

Formula IX wherein $R_1$ and Y are as defined above, and $R_3$' is selected from the group consisting of: hydrogen; a phenol protected group selected from methyl, arylmethyl, $C_1$-$C_4$-alkoxymethyl, unsubstituted or substituted $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, and OSi($R^a$)$_3$ wherein $R^a$ is the same or different and selected from $C_1$-$C_4$-alkyl and phenyl; and (CH$_2$)$_n$NR'R" wherein n is an integer from 2-6, and R' and R" are the same or different and selected from the group consisting of: $C_1$-$C_6$-alkyl, benzyl, and substituted benzyl or are fused to a link —(CH$_2$)$_m$—V—(CH$_2$)$_2$— wherein m is an integer from 1-3, and —V— is —CH$_2$—, —O— or —NR'''— wherein R''' is hydrogen, methyl or ethyl, and wherein $R_3$' and $R_3$ are the same.

4. The process according to claim 3, wherein the sulfonimidoquinone of Formula III

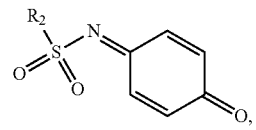

Formula III is treated with a compound of Formula IX$^C$

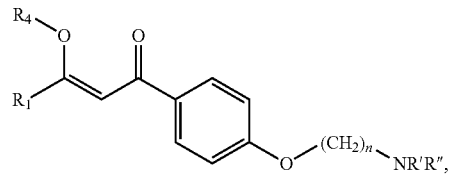

Formula IX$^C$ wherein $R_1$ is as defined above, n is an integer from 2-6 and $R_4$ is selected from the group consisting of:

—Si($R^a$)$_3$ wherein $R^a$ is the same or different and selected from the group consisting of: $C_1$-$C_4$-alkyl and phenyl, —SO$_2$$R^b$ wherein $R^b$ selected from the group consisting of: unsubstituted or fluorinated $C_1$-$C_4$-alkyl, and phenyl, —P(O)(OR$^c$)$_2$ wherein $R^c$ is selected from the group consisting of: $C_1$-$C_4$-alkyl, and phenyl, and R' and R" are the same or different and selected from the group consisting of: $C_1$-$C_6$-alkyl, benzyl, and substituted benzyl, or R' and R" are fused to a link —(CH$_2$)$_m$—V—(CH$_2$)$_2$—wherein m is an integer from 1-3, and —V— is —CH$_2$—, —O— or —NR'''— wherein R''' is hydrogen, methyl or ethyl.

5. The process according to claim 3, wherein in step a), the compound of Formula IX is a compound of Formula XII:

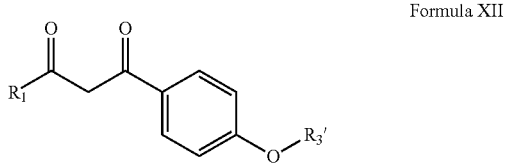

Formula XII wherein R₁ is a $C_1$-$C_8$-alkyl,
R₃' is selected from the group consisting of: hydrogen, a phenol protecting group and $(CH_2)_n NR'R''$ wherein n is an integer from 2-6 and R' and R" are the same or different and selected from the group consisting of: $C_1$-$C_6$-alkyl, benzyl, and substituted benzyl or R' and R" are fused to a link $—(CH_2)_m—V—(CH_2)_2—$ wherein m is an integer from 1-3, and —V— is $—CH_2—$, —O— or —NR'"— wherein R'" is hydrogen, methyl or ethyl,
wherein step a) is performed in the presence of a base selected from the group consisting of: tertiary amines, alkoxides, and hydrides,
and wherein step a) further comprises treating a mixture of the compound of Formula III and the compound of Formula XII with a base selected from the group consisting of: tertiary amines and a Lewis acid selected from titanium cation, tin cation, manganese cation, nickel cation, iron cation, and zinc cation, to give the compound of Formula II$^A$

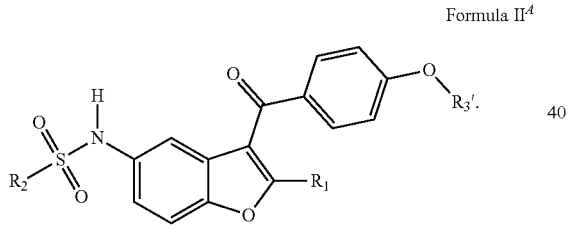

Formula II$^A$

6. A process for the preparation of a compound of Formula V or a salt thereof

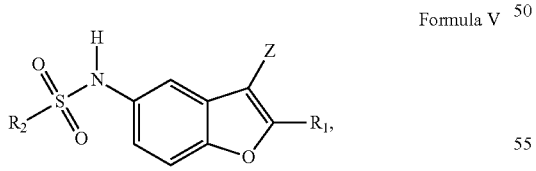

Formula V wherein
R₁ is a $C_1$-$C_8$-alkyl,
R₂ is selected from the group consisting of: $C_1$-$C_8$-alkyl, fluorinated $C_1$-$C_8$-alkyl, phenyl, and para substituted phenyl, and
Z is cyano or C(O)R, wherein
R represents a benzene ring having a halo substituent in none, one or both of the meta positions and having a fluoro, chloro, bromo, iodo, nitro, $C_1$-$C_8$-alkyl, substituted $C_1$-$C_8$-alkyl, hydroxy, $C_1$-$C_8$-alkoxy, substituted $C_1$-$C_8$-alkoxy, $C_1$-$C_8$-alkylamino or substituted $C_1$-$C_8$-alkylamino substituent in the para position,
the process comprising
a) treating a compound of Formula III,

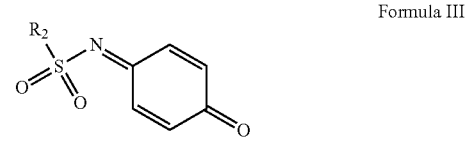

Formula III wherein R₂ is selected from the group consisting of: $C_1$-$C_8$-alkyl, fluorinated $C_1$-$C_8$-alkyl, phenyl, and para substituted phenyl,
with a compound of Formula IV$^A$,

Formula IV$^A$ wherein R₁ is a $C_1$-$C_8$-alkyl, R₂ is selected from the group consisting of: $C_1$-$C_8$-alkyl, fluorinated $C_1$-$C_8$-alkyl, phenyl, and para substituted phenyl, and Y is selected from the group consisting of hydroxy, $C_1$-$C_2$-alkoxy, phenoxy,
—OSi(R$^a$)₃ wherein R$^a$ is the same or different and selected from the group consisting of: $C_1$-$C_4$-alkyl and phenyl,
—OSO₂R$^b$ wherein R$^b$ is selected from the group consisting of unsubstituted or fluorinated $C_1$-$C_4$-alkyl, and phenyl, —OP(O)(OR$^c$)₂ wherein R$^c$ is selected from the group consisting of $C_1$-$C_4$-alkyl, and phenyl, and
wherein Z$^A$ is cyano or C(O)R, wherein R is selected from the group consisting of hydrogen, hydroxyl, $C_1$-$C_4$-alkoxy, benzyloxy, substituted benzyloxy, and NR$^y$R$^z$ wherein R$^y$ and R$^z$ are the same or different and selected from the group consisting of: hydrogen, $C_1$-$C_4$-alkyl, and methoxy, or are fused by $—(CH_2)_m—V—(CH_2)_2—$, wherein m an integer from 1-3 and —V— is $—CH_2—$, —O— or —NR'"—, wherein R'" is hydrogen, methyl or ethyl,
b) treating the compound obtained from step a) with a compound of Formula VI$^A$

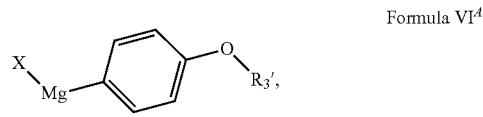

Formula VI$^A$ wherein X represents chloro, bromo or iodo, and R₃' is hydrogen, a phenol protecting group or $(CH_2)_n NR'R''$ wherein n is an integer from 2-6, and R' and R" are the same or different and selected from the group consisting of: $C_1$-$C_6$-alkyl, benzyl, and substituted benzyl or R' and R" are fused to a link $—(CH_2)_m—V—(CH_2)_2—$ wherein m is an integer from 1-3, and —V— is $—CH_2—$, —O— or —NR'"— wherein R'" is hydrogen, methyl or ethyl.

7. The process according to claim 6, wherein in step b) the compound of Formula VI$^A$

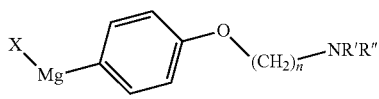

Formula VI$^A$ is used, wherein X is halo, n is an integer from 2-6 and R' and R" are the same or different and selected from the group consisting of: $C_1$-$C_6$-alkyl, benzyl, and substituted benzyl or are fused to alkylene —$(CH_2)_m$—, wherein m is an integer from 4-6, or R' and R" are fused to a link —$(CH_2)_m$—V—$(CH_2)_2$— wherein m is an integer from 1-3, and —V— is —$CH_2$—, —O— or —NR'"—, wherein R'" is hydrogen, methyl or ethyl.

8. A process for the preparation of a compound of Formula V or a salt thereof

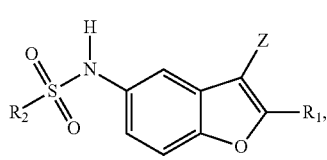

Formula V wherein $R_1$ is a $C_1$-$C_8$-alkyl, $R_2$ is selected from the group consisting of: $C_1$-$C_8$-alkyl, fluorinated $C_1$-$C_8$-alkyl, phenyl, and para substituted phenyl, and Z is cyano or C(O)R, wherein R represents a benzene ring having a halo substituent in none, one or both of the meta positions and having a fluoro, chloro, bromo, iodo, nitro, $C_1$-$C_8$-alkyl, substituted $C_1$-$C_8$-alkyl, hydroxy, $C_1$-$C_8$-alkoxy, substituted $C_1$-$C_8$-alkoxy, $C_1$-$C_8$-alkylamino or substituted $C_1$-$C_8$-alkylamino substituent in the para position, the process comprising a) treating a compound of Formula III

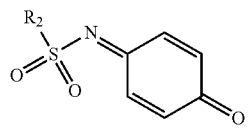

Formula III with a compound of Formula IV$^A$

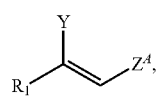

Formula IV$^A$ wherein $R_1$ is a $C_1$-$C_6$-alkyl, $R_2$ is selected from the group consisting of: $C_1$-$C_8$-alkyl, fluorinated $C_1$-$C_8$-alkyl, phenyl, and para substituted phenyl, and Y is selected from the group consisting of: hydroxy, $C_1$-$C_2$-alkoxy, phenoxy, —OSi($R^a$)$_3$ wherein $R^a$ is the same or different and selected from $C_1$-$C_4$-alkyl and phenyl, —OSO$_2R^b$ wherein $R^b$ is selected from unsubstituted or fluorinated $C_1$-$C_4$-alkyl, or phenyl, and —OP(O)(OR$^c$)$_2$ wherein $R^c$ is selected from $C_1$-$C_4$-alkyl, and phenyl, and $Z^A$ is cyano or C(O)R, wherein R is selected from the group consisting of: $C_1$-$C_4$-alkoxy, benzyloxy and substituted benzyloxy, NR$^y$R$^z$ wherein R$^y$ and R$^z$ are the same or different and selected from the group consisting of: hydrogen, $C_1$-$C_4$-alkyl, and methoxy, or are fused by —$(CH_2)_m$—V—$(CH_2)_2$—, wherein m an integer from 1-3 and —V— is —$CH_2$—, —O— or —NR'"—, wherein R'" is hydrogen, methyl or ethyl, b) oxidizing, hydrolysing, or hydrogenolysing the compound resulting from step a) into a compound of Formula VII

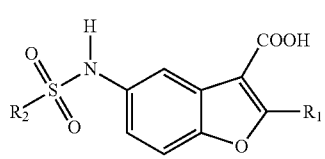

Formula VII c) optionally treating the compound of Formula VII with reactive sulfur, phosphorus, and acyl halogenides to form a compound of Formula VIII

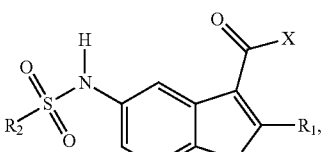

Formula VIII wherein X is selected from the group consisting of: halo and acyl, and d) treating the compound of Formula VIII with a compound of Formula VI$^B$

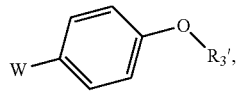

Formula VI$^B$ wherein W represents hydrogen, chloro, bromo or iodo and $R_3$' is hydrogen, a phenol protecting group or $(CH_2)_n$NR'R" wherein n is an integer from 2-6 and R' and R" are the same or different and selected from the group consisting of $C_1$-$C_6$-alkyl, benzyl, and substituted benzyl or R' and R" are fused to a link —$(CH_2)_m$—V—$(CH_2)_2$—, wherein m is an integer from 1-3, and —V— is —$CH_2$—, —O— or —NR'"—, wherein R'" is hydrogen, methyl or ethyl.

9. The process according to claim 3 for the preparation of a compound of Formula II

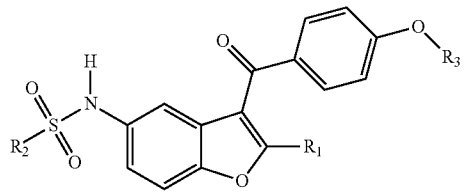

Formula II or a pharmaceutically acceptable salt thereof,
wherein $R_1$ is n butyl, $R_2$ from methyl, and $R_3$ from 3-(dibutylamino)-1-propyl.

10. A process of claim 1, wherein
Formula V comprises dronedarone.

11. A process for the preparation of a pharmaceutical composition comprising dronedarone as active ingredient, comprising the steps of:
a) preparing dronedarone or a pharmaceutically acceptable salt thereof according to the process as defined in claim 1, and
b) admixing the thus prepared dronedarone or pharmaceutically acceptable salt thereof with at least one pharmaceutically acceptable excipient.

12. The process according to claim 11, wherein the at least one pharmaceutically acceptable excipient in step b) is selected from the group consisting of binders, diluents, disintegrating agents, stabilizing agents, preservatives, lubricants, fragrances, flavoring agents, and sweeteners.

13. The process according to claim 1 wherein the compound of Formula V is a compound of Formula II

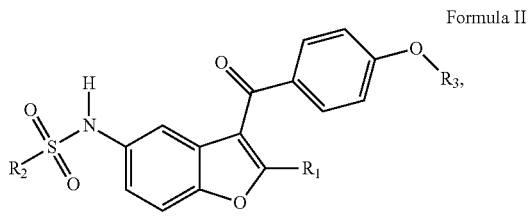

Formula II wherein $R_3$ is $(CH_2)_n NR'R''$, wherein n is an integer from 2 to 6, and R' and R'' are the same or different and are selected from $C_1$-$C_6$-alkyl, benzyl, and substituted benzyl, or R' and R'' are fused by —$(CH_2)_m$—V—$(CH_2)_2$— wherein m is an integer from 1-3, and —V— is —$CH_2$—, —O— or —NR'''— wherein R''' is hydrogen, methyl or ethyl,
the process comprising
a) treating the sulfonimidoquinone of Formula III

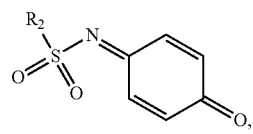

Formula III wherein $R_2$ is as defined above,
with a compound of Formula IX in enolic or ketonic tautomeric form,

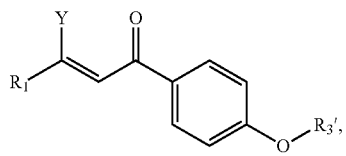

Formula IX wherein $R_1$ and Y are as defined above, and
and wherein $R_3'$ is hydrogen,
to give a compound of Formula $II^A$

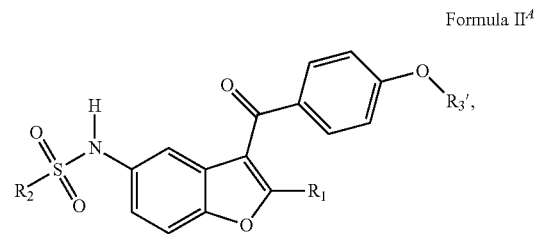

Formula $II^A$ and
b) converting the compound of Formula $II^A$ into the compound of Formula II by:
substituting the phenolic hydroxyl group by the compound of formula L-$(CH_2)_n$-A, wherein
L is a leaving group selected from the group consisting of: halo, $C_1$-$C_8$-acyl, $C_1$-$C_8$-alkylsulfonyl, fluorinated $C_1$-$C_8$-alkylsulfonyl, benzenesulfonyl, para substituted benzenesulfonyl, and camphor-10-sulfonyl;
n is an integer from 2-6;
A is a leaving group selected from the group consisting of: halo, $C_1$-$C_8$-acyl, $C_1$-$C_8$-alkylsulfonyl, fluorinated $C_1$-$C_8$-alkylsulfonyl, benzenesulfonyl, para substituted benzenesulfonyl; camphor-10-sulfonyl, and NR'R'' wherein n is an integer from 2-6, and R' and R'' are the same or different and selected from the group consisting of: $C_1$-$C_6$-alkyl, benzyl, and substituted benzyl, or are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl, wherein L and A represent leaving groups in reactions of nucleophilic substitution and are the same or different, to give the following compound:

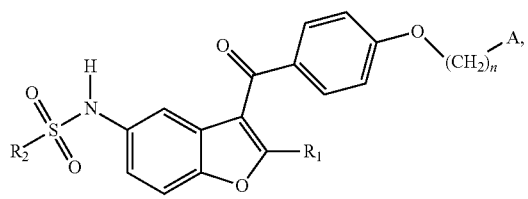

wherein A is NR'R'',
or, if A is not NR'R'', further treating with an amine HNR'R'' wherein n is an integer from 2-6 and R' and R'' are the same or different and selected from $C_1$-$C_8$-alkyl, benzyl, substituted benzyl or R' and R'' are fused to a link —$(CH_2)_m$—V—$(CH_2)_2$— wherein m is an integer from 1-3, and —V— is —$CH_2$—, —O— or —NR'''— wherein R''' is hydrogen, methyl or ethyl.

14. The process according to claim 1 wherein the compound of Formula V is a compound of Formula II Formula II

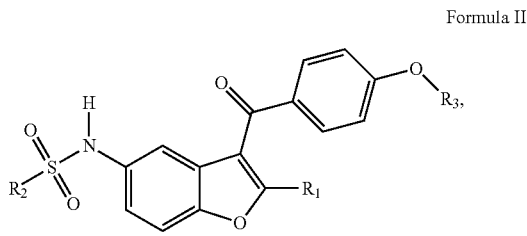

wherein $R_3$ is $(CH_2)_n NR'R''$, wherein n is an integer from 2 to 6, and R' and R'' are the same or different and selected from the group consisting of $C_1$-$C_6$ alkyl, benzyl, and substituted benzyl, or R' and R'' are fused by —$(CH_2)_m$—V—$(CH_2)_2$— wherein m is an integer from 1-3, and —V— is —$CH_2$—, —O— or —NR'''— wherein R''' is hydrogen, methyl, or ethyl,
the process comprising
a) treating the sulfonimidoquinone of Formula III Formula III

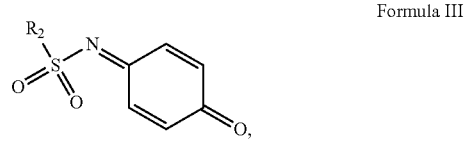

wherein $R_2$ is as defined above,
with a compound of Formula IX in enolic or ketonic tautomeric form, Formula IX

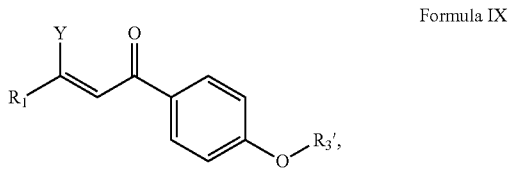

wherein $R_1$ and Y are as defined above, and
$R_3'$ is a phenol protecting group selected from the group consisting of methyl, arylmethyl, $C_1$-$C_4$-alkoxymethyl, unsubstituted or substituted $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, and $OSi(R^a)_3$ wherein $R^a$ is the same or different and selected from the group consisting of $C_1$-$C_4$-alkyl and phenyl;
to give a compound of Formula $II^A$ Formula $II^A$

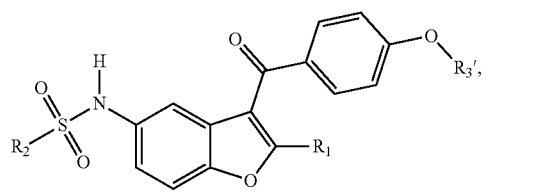

and
b) converting the compound of Formula $II^A$ into the compound of Formula II by:

deprotecting with corresponding reagents to give the following compound:

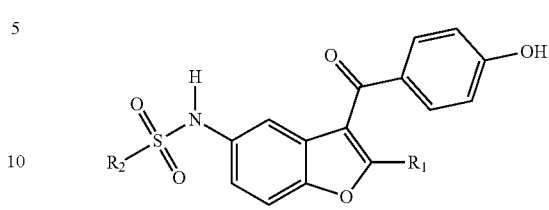

substituting the phenolic hydroxyl group by the compound of formula L-$(CH_2)_n$-A,
wherein
L is a leaving group selected from the group consisting of: halo, $C_1$-$C_8$-acyl, $C_1$-$C_8$-alkylsulfonyl, fluorinated $C_1$-$C_8$-alkylsulfonyl, benzenesulfonyl, para substituted benzenesulfonyl, and camphor-10-sulfonyl;
n is an integer from 2-6;
A is a leaving group selected from the group consisting of: halo, $C_1$-$C_8$-acyl, $C_1$-$C_8$-alkylsulfonyl, fluorinated $C_1$-$C_8$-alkylsulfonyl, benzenesulfonyl, para substituted benzenesulfonyl, camphor-10-sulfonyl, and NR'R'',
wherein R' and R'' are the same or different and selected from the group consisting of: $C_1$-$C_6$-alkyl, benzyl, and substituted benzyl, or R' and R'' are fused to a link —$(CH_2)_m$—V—$(CH_2)_2$— wherein m is an integer from 1 to 3, and —V— is —$CH_2$—, —O—, or —NR'''— wherein R''' is hydrogen, methyl, or ethyl,
wherein L and A represent leaving groups in reactions of nucleophilic substitution and are the same or different, to give the following compound:

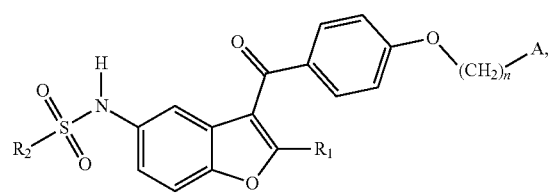

wherein A is NR'R'',
and wherein if A is not NR'R'', further treating with an amine HNR'R'' wherein n is an integer from 2-6 and R' and R'' are the same or different and selected from the group consisting of: $C_1$-$C_6$-alkyl, benzyl, and substituted benzyl, or R' and R'' are fused to a link —$(CH_2)_m$—V—$(CH_2)_2$— wherein m is an integer from 1-3, and —V— is —$CH_2$—, —O—, or —NR'''— wherein R''' is hydrogen, methyl, or ethyl.

* * * * *